United States Patent
Ayton et al.

(10) Patent No.: US 9,095,426 B2
(45) Date of Patent: Aug. 4, 2015

(54) METHOD AND DEVICE FOR COMPACTING AN INTRAOCULAR LENS

(75) Inventors: Ian Ayton, Santa Ynez, CA (US); Scott Evans, Santa Ana, CA (US); Tuan Nguyen, Orange, CA (US)

(73) Assignee: Visiogen, Inc., Santa Ana, CA (US)

( * ) Notice: Subject to any disclaimer, the term of this patent is extended or adjusted under 35 U.S.C. 154(b) by 924 days.

(21) Appl. No.: 11/844,964

(22) Filed: Aug. 24, 2007

(65) Prior Publication Data

US 2008/0045971 A1 Feb. 21, 2008

Related U.S. Application Data

(62) Division of application No. 10/637,376, filed on Aug. 8, 2003, now Pat. No. 7,615,056.

(60) Provisional application No. 60/448,190, filed on Feb. 14, 2003.

(51) Int. Cl.
*A61F 9/00* (2006.01)
*A61F 2/16* (2006.01)

(52) U.S. Cl.
CPC ............ *A61F 2/1678* (2013.01); *A61F 2/1648* (2013.01); *A61F 2250/0021* (2013.01)

(58) Field of Classification Search
CPC ... A61F 2/1648; A61F 2/1662; A61F 2/1672; A61F 2/1678
USPC ......................... 606/107; 623/4.1, 6.11, 6.12, 623/6.32–6.36; 206/5.1, 316.1
See application file for complete search history.

(56) References Cited

U.S. PATENT DOCUMENTS

| | | | |
|---|---|---|---|
| 4,240,163 A | 12/1980 | Galin | |
| 4,409,691 A | 10/1983 | Levy | |
| 4,636,210 A | 1/1987 | Hoffer | |
| 4,655,770 A | 4/1987 | Gupta et al. | |
| 4,666,445 A | 5/1987 | Tillay | |

(Continued)

FOREIGN PATENT DOCUMENTS

| | | |
|---|---|---|
| DE | 19501444 | 7/1996 |
| DE | 10015472 | 11/2001 |

(Continued)

OTHER PUBLICATIONS

Tsutomu Hara et al., "Accommodative Intraocular Lens with Spring Action Part 1. Design and Placement in an Excised Animal Eye," Opthalmic Surgery, Feb. 1990, vol. 21, No. 2, pp. 128-133.

(Continued)

*Primary Examiner* — Kathleen Holwerda
*Assistant Examiner* — Sarah Simpson

(57) ABSTRACT

Disclosed is an apparatus for compacting an intraocular lens. The apparatus comprises a lens compactor having a first configuration for retaining the intraocular lens in an unstressed condition and a second configuration in which the compactor stresses the lens into an at least partially compacted condition without advancing the lens along an injection axis of the compactor. The compactor accomplishes this by applying a compacting force in a direction generally orthogonal to the optical axis of the lens. The compactor is responsive to a compactor actuator that is movable by a user to change the compactor from the first configuration to the second configuration. Additional apparatus and methods are disclosed as well.

18 Claims, 26 Drawing Sheets

(56) References Cited

U.S. PATENT DOCUMENTS

| | | | | |
|---|---|---|---|---|
| 4,681,102 A | | 7/1987 | Bartell | |
| 4,702,244 A | | 10/1987 | Mazzocco | |
| 4,731,079 A | | 3/1988 | Stoy | |
| 4,790,847 A | | 12/1988 | Woods | |
| 4,834,094 A | | 5/1989 | Patton et al. | |
| 4,836,201 A | * | 6/1989 | Patton et al. | 606/107 |
| 4,842,601 A | | 6/1989 | Smith | |
| 4,862,885 A | | 9/1989 | Cumming | |
| 4,883,485 A | | 11/1989 | Patel | |
| 4,888,012 A | | 12/1989 | Horn et al. | |
| 4,892,543 A | | 1/1990 | Turley | |
| 4,919,130 A | | 4/1990 | Stoy et al. | |
| 4,932,966 A | | 6/1990 | Christie et al. | |
| 4,963,148 A | | 10/1990 | Sulc et al. | |
| 4,994,082 A | | 2/1991 | Richards et al. | |
| 5,098,439 A | | 3/1992 | Hill et al. | |
| 5,123,905 A | | 6/1992 | Kelman | |
| 5,171,319 A | | 12/1992 | Keates et al. | |
| 5,190,552 A | | 3/1993 | Kelman | |
| 5,190,553 A | | 3/1993 | Kanert et al. | |
| 5,275,604 A | | 1/1994 | Rheinish et al. | |
| 5,275,623 A | | 1/1994 | Sarfarazi | |
| 5,281,227 A | | 1/1994 | Sussman | |
| 5,326,347 A | | 7/1994 | Cumming | |
| 5,354,335 A | | 10/1994 | Lipshitz et al. | |
| 5,425,734 A | | 6/1995 | Blake | |
| 5,443,506 A | | 8/1995 | Garabet | |
| 5,468,246 A | | 11/1995 | Blake | |
| 5,474,562 A | | 12/1995 | Orchowski | |
| 5,476,514 A | | 12/1995 | Cumming | |
| 5,494,484 A | | 2/1996 | Feingold | |
| 5,496,328 A | | 3/1996 | Nakajima et al. | |
| 5,499,987 A | | 3/1996 | Feingold | |
| 5,507,806 A | | 4/1996 | Blake | |
| 5,578,081 A | | 11/1996 | McDonald | |
| 5,607,472 A | | 3/1997 | Thompson | |
| 5,616,148 A | | 4/1997 | Eagles et al. | |
| 5,620,450 A | | 4/1997 | Eagles et al. | |
| 5,653,754 A | | 8/1997 | Nakajima et al. | |
| 5,728,102 A | | 3/1998 | Feingold | |
| 5,735,858 A | | 4/1998 | Makker et al. | |
| 5,800,442 A | | 9/1998 | Wolf et al. | |
| 5,807,400 A | | 9/1998 | Chambers et al. | |
| 5,860,984 A | | 1/1999 | Chambers et al. | |
| 5,873,879 A | | 2/1999 | Figueroa et al. | |
| 5,876,440 A | | 3/1999 | Feingold | |
| 5,921,989 A | | 7/1999 | Deacon et al. | |
| 5,928,245 A | | 7/1999 | Wolf et al. | |
| 5,941,886 A | | 8/1999 | Feingold | |
| 5,944,725 A | | 8/1999 | Cicenas et al. | |
| 5,947,975 A | | 9/1999 | Kikuchi et al. | |
| 5,968,094 A | | 10/1999 | Werblin et al. | |
| 5,984,962 A | | 11/1999 | Anello et al. | |
| 6,010,510 A | | 1/2000 | Brown et al. | |
| 6,013,101 A | | 1/2000 | Israel | |
| 6,056,758 A | | 5/2000 | Vidal et al. | |
| 6,083,230 A | | 7/2000 | Makker et al. | |
| 6,106,554 A | | 8/2000 | Bretton | |
| 6,117,171 A | | 9/2000 | Skottun | |
| 6,129,733 A | | 10/2000 | Brady et al. | |
| 6,162,229 A | | 12/2000 | Feingold et al. | |
| 6,176,878 B1 | | 1/2001 | Gwon et al. | |
| 6,179,843 B1 | | 1/2001 | Weiler | |
| 6,197,058 B1 | | 3/2001 | Portney | |
| 6,197,059 B1 | | 3/2001 | Cumming | |
| 6,203,549 B1 | | 3/2001 | Waldock | |
| 6,217,612 B1 | | 4/2001 | Woods | |
| 6,228,094 B1 | | 5/2001 | Erdman | |
| 6,231,603 B1 | | 5/2001 | Lang et al. | |
| 6,258,123 B1 | | 7/2001 | Young et al. | |
| 6,280,449 B1 | | 8/2001 | Blake | |
| 6,280,471 B1 | | 8/2001 | Peyman et al. | |
| RE37,387 E | | 9/2001 | Brady et al. | |
| 6,283,975 B1 | | 9/2001 | Glick et al. | |
| 6,299,641 B1 | | 10/2001 | Woods | |
| 6,334,862 B1 | | 1/2002 | Vidal et al. | |
| 6,386,357 B1 | * | 5/2002 | Egawa | 206/5.1 |
| 6,423,094 B1 | | 7/2002 | Sarfarazi | |
| 6,443,985 B1 | | 9/2002 | Woods | |
| 6,450,642 B1 | | 9/2002 | Jethmalani et al. | |
| 6,454,802 B1 | | 9/2002 | Bretton et al. | |
| 6,464,725 B2 | | 10/2002 | Skotton | |
| 6,468,282 B2 | * | 10/2002 | Kikuchi et al. | 606/107 |
| 6,488,708 B2 | | 12/2002 | Sarfarazi | |
| 6,497,708 B1 | * | 12/2002 | Cumming | 606/107 |
| 6,500,181 B1 | * | 12/2002 | Portney | 606/107 |
| 6,503,275 B1 | | 1/2003 | Cumming | |
| 6,551,354 B1 | | 4/2003 | Ghazizadeh et al. | |
| 6,558,420 B2 | | 5/2003 | Green | |
| 6,605,093 B1 | | 8/2003 | Blake | |
| 6,761,737 B2 | | 7/2004 | Zadno-azizi et al. | |
| 6,764,511 B2 | | 7/2004 | Zadno-azizi et al. | |
| 6,786,934 B2 | | 9/2004 | Zadno-azizi et al. | |
| 6,818,158 B2 | | 11/2004 | Pham et al. | |
| 6,846,326 B2 | | 1/2005 | Zadno-azizi et al. | |
| 6,858,040 B2 | | 2/2005 | Nguyen et al. | |
| 6,884,261 B2 | | 4/2005 | Zadno-azizi et al. | |
| 6,899,732 B2 | | 5/2005 | Zadno-azizi et al. | |
| 6,923,815 B2 | | 8/2005 | Brady et al. | |
| 7,041,134 B2 | | 5/2006 | Nguyen et al. | |
| 7,087,080 B2 | | 8/2006 | Zadno-azizi et al. | |
| 7,097,660 B2 | | 8/2006 | Portney | |
| 7,118,596 B2 | | 10/2006 | Zadno-azizi et al. | |
| 7,125,422 B2 | | 10/2006 | Woods et al. | |
| 7,198,640 B2 | | 4/2007 | Nguyen | |
| 7,226,455 B2 | * | 6/2007 | Jeannin et al. | 606/107 |
| 7,226,478 B2 | | 6/2007 | Ting et al. | |
| 7,452,362 B2 | | 11/2008 | Zadno-azizi et al. | |
| 7,452,378 B2 | | 11/2008 | Zadno-azizi et al. | |
| 7,615,056 B2 | | 11/2009 | Ayton et al. | |
| 7,645,300 B2 | | 1/2010 | Tsai | |
| 2001/0020171 A1 | | 9/2001 | Heyman et al. | |
| 2002/0002404 A1 | | 1/2002 | Sarfarazi | |
| 2002/0004682 A1 | | 1/2002 | Zhou et al. | |
| 2002/0077633 A1 | | 6/2002 | Kikuchi et al. | |
| 2002/0082609 A1 | | 6/2002 | Green | |
| 2002/0107568 A1 | * | 8/2002 | Zadno-Azizi et al. | 623/6.37 |
| 2002/0138140 A1 | | 9/2002 | Hanna | |
| 2002/0156486 A1 | * | 10/2002 | Nadel | 606/107 |
| 2002/0188351 A1 | | 12/2002 | Laguette | |
| 2003/0018384 A1 | | 1/2003 | Valyunin et al. | |
| 2003/0078657 A1 | | 4/2003 | Zadno-azizi et al. | |
| 2003/0078658 A1 | | 4/2003 | Zadno-azizi | |
| 2003/0114927 A1 | | 6/2003 | Nagamoto | |
| 2003/0158560 A1 | | 8/2003 | Portney | |
| 2003/0187504 A1 | | 10/2003 | Weinschenk, III et al. | |
| 2004/0059343 A1 | | 3/2004 | Shearer et al. | |
| 2004/0160575 A1 | | 8/2004 | Ayton et al. | |
| 2005/0182419 A1 | | 8/2005 | Tsai | |
| 2005/0228401 A1 | | 10/2005 | Zadno-azizi et al. | |
| 2005/0234547 A1 | | 10/2005 | Nguyen et al. | |
| 2005/0251236 A1 | | 11/2005 | Jeannin et al. | |
| 2006/0100703 A1 | | 5/2006 | Evans et al. | |
| 2006/0178741 A1 | | 8/2006 | Zadno-azizi et al. | |
| 2006/0184244 A1 | | 8/2006 | Nguyen et al. | |
| 2006/0259139 A1 | | 11/2006 | Zadno-azizi et al. | |
| 2006/0271187 A1 | | 11/2006 | Zadno-azizi et al. | |
| 2007/0027540 A1 | | 2/2007 | Zadno-azizi et al. | |
| 2007/0032866 A1 | | 2/2007 | Portney | |
| 2007/0050023 A1 | | 3/2007 | Bessiere et al. | |
| 2007/0050025 A1 | | 3/2007 | Nguyen et al. | |
| 2008/0027461 A1 | | 1/2008 | Vaquero et al. | |
| 2008/0125790 A1 | | 5/2008 | Tsai et al. | |
| 2009/0005788 A1 | | 1/2009 | Rathert | |
| 2009/0112313 A1 | | 4/2009 | Mentak | |
| 2009/0234366 A1 | | 9/2009 | Tsai et al. | |
| 2010/0076449 A1 | | 3/2010 | Tsai | |

FOREIGN PATENT DOCUMENTS

| | | |
|---|---|---|
| EP | 0162573 | 11/1985 |
| EP | 0269288 | 6/1988 |
| EP | 0337390 A2 | 10/1989 |
| EP | 0336877 | 10/1993 |

(56) References Cited

FOREIGN PATENT DOCUMENTS

| | | |
|---|---|---|
| EP | 1114623 | 11/2001 |
| EP | 1481652 | 12/2004 |
| EP | 1736118 | 12/2006 |
| FR | 2900570 | 11/2007 |
| JP | S61-279241 | 12/1986 |
| JP | 02-126847 | 5/1990 |
| JP | H03-137325 | 6/1991 |
| WO | WO 95/13022 | 5/1995 |
| WO | WO 96/29956 | 10/1996 |
| WO | WO 98/12969 | 4/1998 |
| WO | WO 99/20206 | 4/1999 |
| WO | WO 99/21513 | 6/1999 |
| WO | WO 00/21467 | 4/2000 |
| WO | WO 00/27315 | 5/2000 |
| WO | WO 00/61036 | 10/2000 |
| WO | WO 00/66037 | 11/2000 |
| WO | WO 01/19289 | 3/2001 |
| WO | WO 01/34067 | 5/2001 |
| WO | WO 01/64136 | 9/2001 |
| WO | WO 01/66042 | 9/2001 |
| WO | WO 0187186 A1 * | 11/2001 |
| WO | WO 03/015657 | 2/2003 |
| WO | WO 04/000171 | 12/2003 |
| WO | WO 2004/073560 | 9/2004 |
| WO | WO 2007/080868 | 7/2007 |

OTHER PUBLICATIONS

U.S. Appl. No. 12/258,339, filed Oct. 24, 2008.
English Translation of Office Action dated Apr. 24, 2009 and issued in related Japanese Patent Application No. 2006-503503.
International Search Report and Written Opinion of the International Searching Authority, mailed May 18, 2005, in related international application No. PCT/US2004/004033.
U.S. Appl. No. 12/258,339, filed Oct. 24, 2008 and its prosecution history.

* cited by examiner

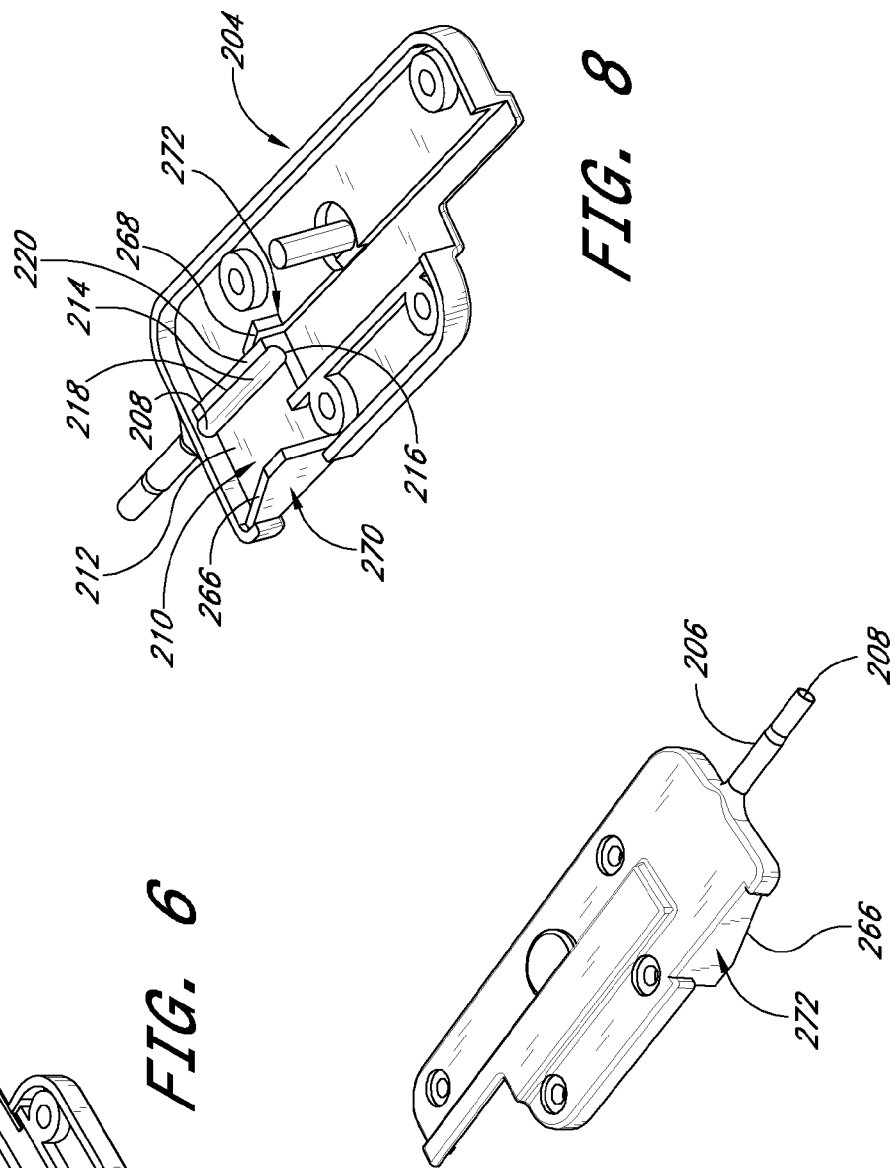

METHOD AND DEVICE FOR COMPACTING AN INTRAOCULAR LENS

RELATED APPLICATIONS

This application is a divisional application of U.S. patent application Ser. No. 10/637,376, filed Aug. 8, 2003, now U.S. Pat. No. 7,615,056 titled METHOD AND DEVICE FOR COMPACTING AN INTRAOCULAR LENS, which claims the benefit under 35 U.S.C. §119(e) of U.S. Provisional Patent Application Ser. No. 60/448,190, filed Feb. 14, 2003, titled METHOD AND DEVICE FOR FOLDING AN ACCOMMODATING INTRAOCULAR LENS. The entire contents of both of the above-mentioned patent applications are hereby incorporated by reference herein and made a part of this specification.

BACKGROUND OF THE INVENTION

1. Field of the Invention

Various embodiments disclosed herein pertain to insertion of intraocular lenses into the eye of a patient, as well as methods and devices for preparing an intraocular lens for insertion, and for achieving the insertion itself.

2. Description of the Related Art

Artificial intraocular lenses are often implanted to replace or supplement the natural crystalline lens. Such a lens may be implanted where the natural lens has developed cataracts or has lost elasticity to create a condition of presbyopia. Implantation devices have been developed to roll or fold an intraocular lens, and/or assist in implanting a rolled or folded lens through a small incision in the patient's eye. However, these known implantation devices suffer from various drawbacks, many of which are addressed by certain embodiments disclosed herein.

SUMMARY OF THE INVENTION

One aspect of the invention is an apparatus for compacting an intraocular lens. The apparatus comprises a lens compactor having a first configuration for retaining the intraocular lens in a substantially unstressed condition and a second configuration in which the compactor stresses the lens into an at least partially compacted condition without advancing the lens along an injection axis of the compactor. The compactor accomplishes this by applying a compacting force in a direction generally orthogonal to the optical axis of the lens. The compactor is responsive to a compactor actuator that is movable by a user to change the compactor from the first configuration to the second configuration.

Another aspect of the invention is a method of delivering an intraocular lens into an eye. The method comprises providing an intraocular lens in a housing which has been sterilized, and ejecting the intraocular lens into the eye without opening the housing. In one embodiment, the intraocular lens may comprise an accommodating intraocular lens.

Another aspect of the invention is a method of compacting an accommodating intraocular lens. The method comprises providing the accommodating intraocular lens within a chamber in an uncompacted state, and compacting the accommodating intraocular lens by relatively moving portions of walls of the chamber to alter the shape of the chamber.

Another aspect of the invention is a method of manufacturing an apparatus for delivering an intraocular lens. The method comprises providing a housing and a lens compactor within the housing, and positioning an intraocular lens within the housing such that the lens is compacted upon actuation of the lens compactor. The method further comprises assembling an injector which includes the housing and the lens compactor, and sterilizing the injector, including the housing, the lens compactor and the intraocular lens, together as a single unit.

Another aspect of the invention is an apparatus for manipulating an accommodating intraocular lens having first and second viewing elements with respective optical axes that are substantially aligned. The apparatus comprises a lens compactor having first and second surfaces for engaging the first and second viewing elements. The surfaces are moveable relative to one another to relatively move the viewing elements such that the optical axes are displaced relative to each other.

Another aspect of the invention is an apparatus for manipulating an accommodating intraocular lens having first and second viewing elements with respective optical axes that are substantially aligned. The apparatus comprises a lens compactor having first and second surfaces for engaging the first and second viewing elements. The surfaces are moveable relative to one another to relatively move the viewing elements such that the optical axes are displaced relative to each other. The compactor further comprises a moveable first compacting element which applies force to the viewing elements while the optical axes are displaced such that the viewing elements are compacted against an opposing second compacting element.

Another aspect of the invention is an apparatus comprising a sterile package and an injector disposed within the package. The injector comprises a housing, a lens compactor disposed within the housing, and an intraocular lens disposed within the lens compactor and positioned such the lens is compacted upon actuation of the lens compactor.

Another aspect of the invention is an apparatus for delivering an intraocular lens. The apparatus comprises a lens compactor. The intraocular lens is disposed within the lens compactor and positioned such the lens is compacted upon actuation of the lens compactor. The apparatus further comprises a delivery probe in communication with the lens compactor. The delivery probe defines a delivery axis. The lens compactor comprises a compacting element which contacts the intraocular lens and is moveable in a first direction generally parallel to the injection axis and in a second direction generally orthogonal to the injection axis.

All of these aspects and embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 6 is a perspective view of the lower housing of the apparatus of FIG. 3.

FIG. 7 is a second perspective view of the lower housing of the apparatus of FIG. 3.

FIG. 8 is a third perspective view of the lower housing of the apparatus of FIG. 3.

DETAILED DESCRIPTION OF THE PREFERRED EMBODIMENT

Figure 1:
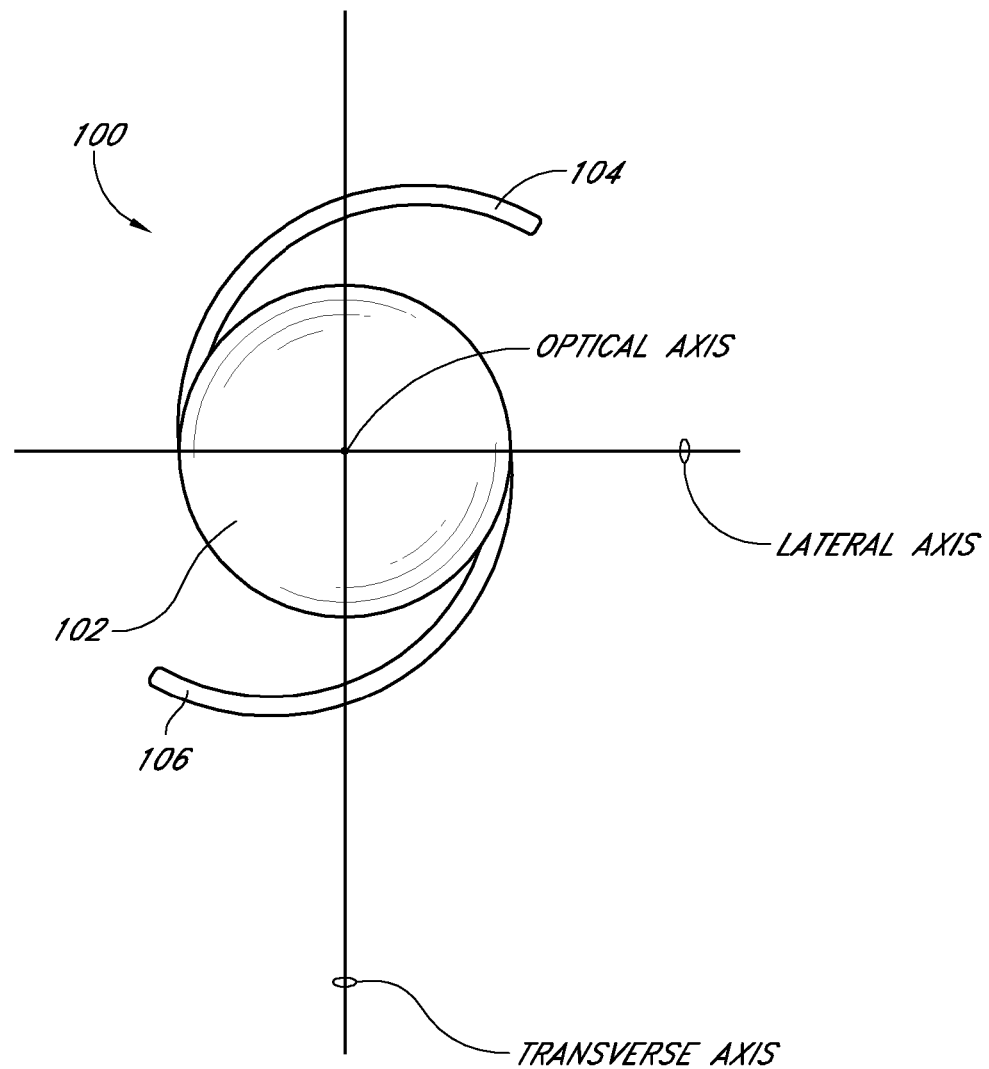
FIG. 1 is a front view of one type of single-lens IOL.
Figure 2:
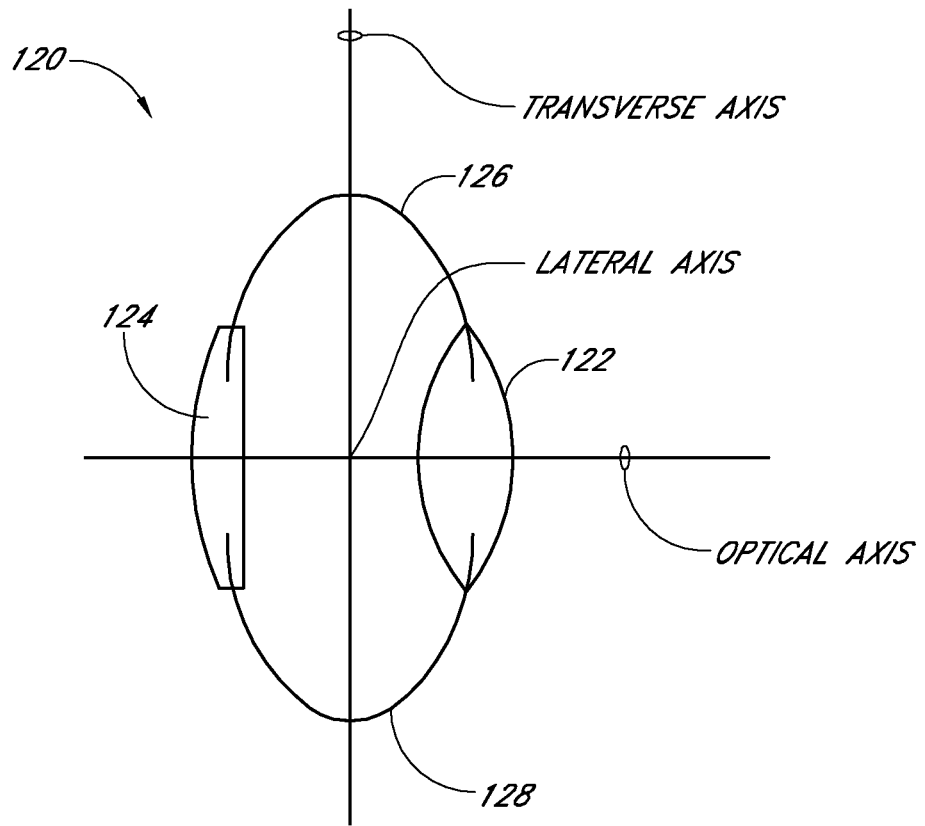
FIG. 2 is a side view of one type of multiple-lens IOL.

FIGS. 1 and 2 depict two known types of intraocular lenses ("IOLs") which are suitable for implantation in a human or animal eye to replace or supplement the natural crystalline lens. An IOL may be implanted, for example, when the natural lens has developed cataracts or has lost elasticity to create a condition of presbyopia.

FIG. 1 is front view of a conventional single-lens IOL 100 comprising an optic 102 to which are connected two or more haptics 104, 106. The optic 102 typically has a refractive power which is selected to replace or adjust the optical performance of the natural lens. The haptics 104, 106 comprise spring-like members which fix the optic in an appropriate location (e.g., inside the ciliary capsule or between the cornea and iris). The IOL 100 has an optical axis generally orthogonal to and centered on the optic; accordingly, in FIG. 1 the optical axis is depicted as a point. In addition, the IOL 100 has a transverse axis orthogonal to the optical axis and passing through arbitrarily chosen top and bottom points of the IOL 100, and a lateral axis orthogonal to the optical and transverse axes, and passing through arbitrarily chosen left and right points of the IOL 100. (The top, bottom, left and right positions are said to be "arbitrarily chosen" because the IOL 100 can be employed in a variety of orientations within the eye, so long as the optical axis is substantially coincident with the optical axis of the eye itself.)

FIG. 2 is a side view of a dual- or multiple-lens IOL 120 comprising first and second viewing elements 122, 124 which are interconnected by two or more biasing members 126, 128. One or both of the viewing elements 122, 124 may comprise an optic having refractive power. An IOL of this type is typically implanted in the ciliary capsule such that the biasing members maintain one of the viewing elements 122, 124 against the anterior region of the ciliary capsule, and the other of the viewing elements 122, 124 against the posterior region of the ciliary capsule. The biasing members 126, 128 may be constructed to have spring-like properties to permit the separation between the viewing elements 122, 124 to change in response to changes in the shape of the ciliary capsule that occur during accommodation.

Like the single-lens IOL 100, the multiple-lens IOL 120 has an optical axis, transverse axis and lateral axis, arranged depicted in FIG. 2. In the unstressed configuration shown in FIG. 2, the optical axes of the individual viewing elements 122, 124 are substantially coincident with the optical axis of the IOL 120 itself. However, as discussed below the optical axes of the individual viewing elements 122, 124 may be made non-coincident or non-coaxial during compaction of the IOL 120.

Various types of multiple-lens IOLs are disclosed in U.S. Patent Application Publication No. US 2002/0107568 A1, published on Aug. 8, 2002, titled ACCOMMODATING INTRAOCULAR LENS SYSTEM, and U.S. Patent Application Publication No. US 2003/0074060 A1, published on Apr. 17, 2003, titled METHOD OF PREPARING AN INTRAOCULAR LENS FOR IMPLANTATION. The entire contents of the above-mentioned publications are hereby incorporated by reference herein and made a part of this specification.

Intraocular lenses are typically implanted (after any removal of the natural lens) by first folding or rolling the IOL. The folded/rolled IOL is then inserted into the desired location in the eye by passing the IOL through one or more incisions made in the cornea, sclera and/or ciliary capsule. Once in place, the natural resilience of the IOL causes it to return, either partially or completely, to its original unrolled/unfolded state, whereupon the IOL can function as desired to improve the patient's vision.

FIGS. 3-20 depict one embodiment of an apparatus 200 for compacting and/or inserting an intraocular lens. The depicted apparatus 200 (as well as the other embodiments depicted and/or described herein) may, but need not, be employed to compact and/or insert an intraocular lens, including without limitation IOLs of the types depicted in FIG. 1 or FIG. 2, those described in the publications mentioned above, or any suitable single- or multiple-lens IOL.

Figure 3:
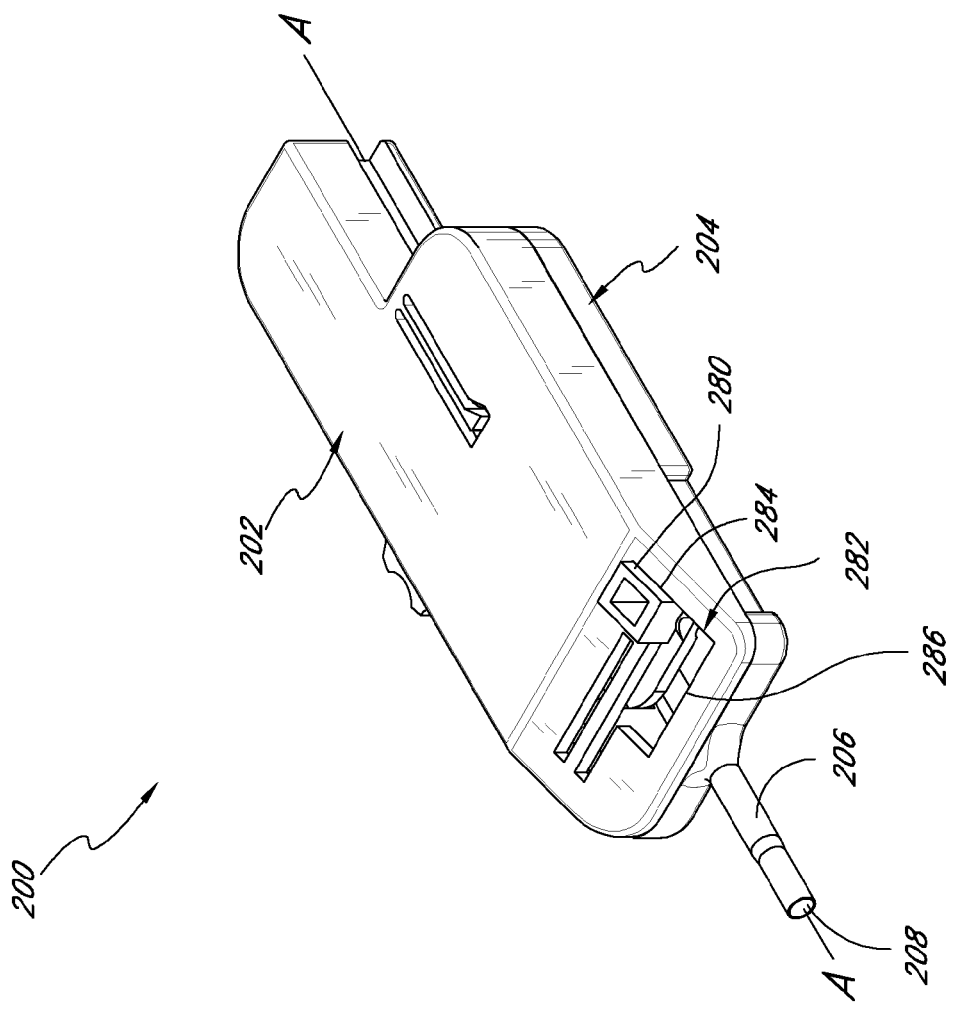
FIG. 3 is a perspective view of one embodiment of an apparatus for compacting and/or inserting an intraocular lens.
Figure 4:
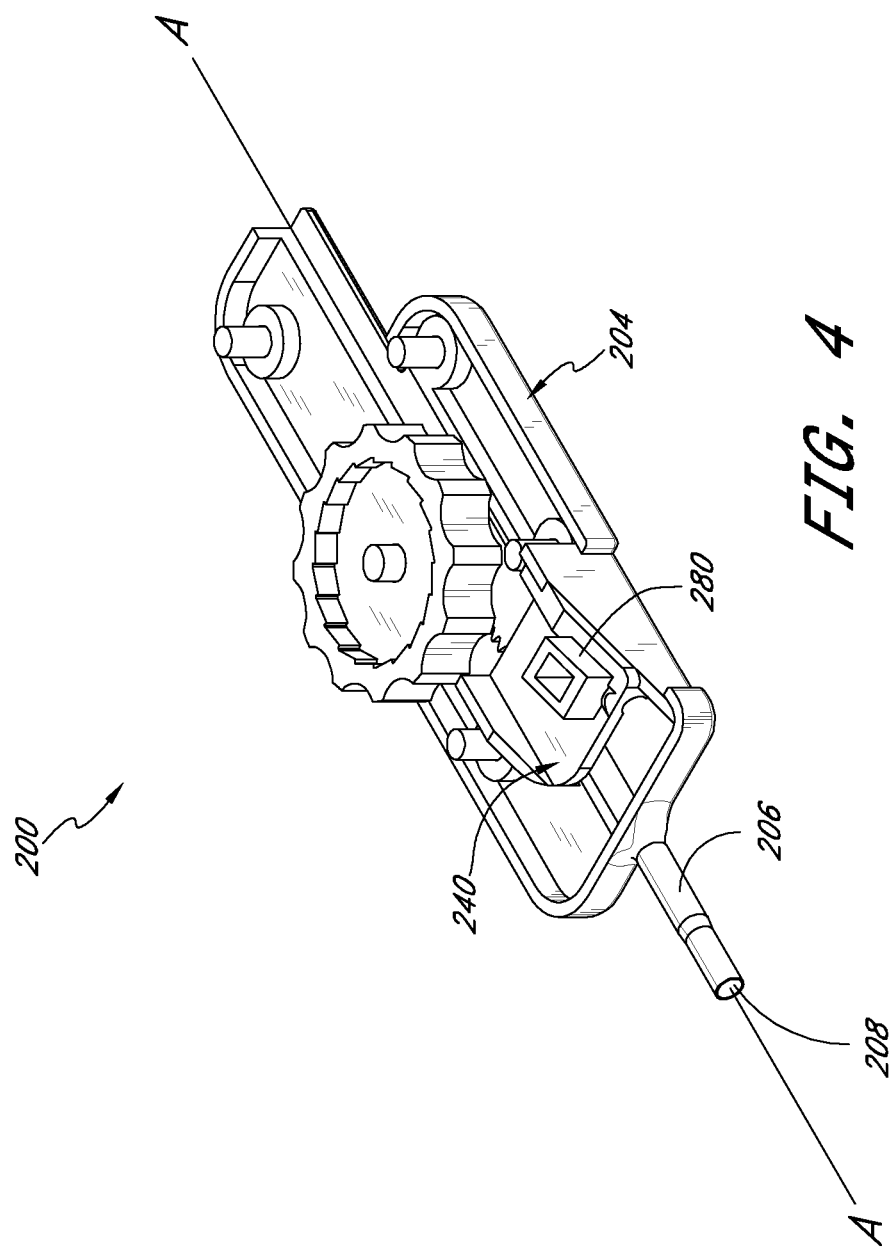
FIG. 4 is a perspective view of the apparatus of FIG. 3, with the upper housing portion removed for clarity.
Figure 5:
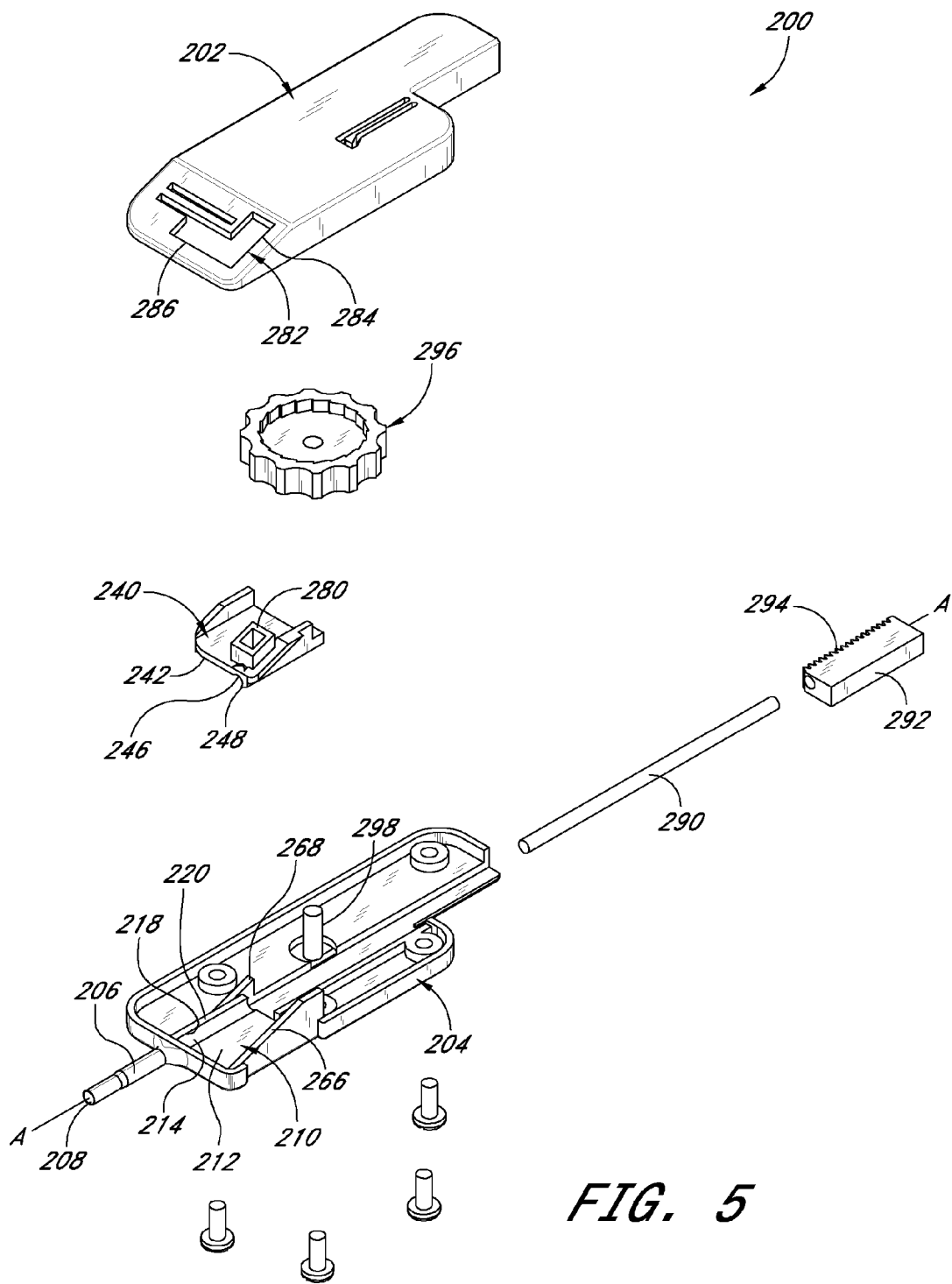
FIG. 5 is an exploded view of the apparatus of FIG. 3.

With reference now to FIGS. 3-5, the apparatus 200 preferably comprises an upper housing 202 and a lower housing 204 which cooperate to enclose and support the components of the apparatus 200. The lower housing 204 preferably forms a delivery probe 206 which in turn defines a delivery lumen 208; both the delivery probe 206 and lumen 208 extend along a longitudinally-oriented delivery or injection axis A-A of the apparatus 200. The lower housing 204 also preferably forms a lower lens compactor or lower compacting element 210 comprising a lower engagement face or wall 212 and a lower insertion channel 214 which extends along the delivery axis A-A.

As best seen in FIG. 8, the lower engagement face 212 preferably comprises a generally flat surface which defines a plane extending generally parallel to (or intercepting) the delivery axis A-A. The lower insertion channel 214 is preferably a partial cylinder in shape, with an inner surface 216 which extends from the lower engagement face 212 to a lower channel edge 218 which preferably extends generally parallel to the delivery axis A-A. The lower insertion channel 214 preferably comprises a partial rearward extension, along the delivery axis A-A, of the inner surface of the delivery lumen 208. From the lower channel edge 218 a lower support surface 220 extends in a direction opposite the lower engagement face 212, while forming a generally flat surface which defines a plane extending preferably generally parallel to the face 212.

Figure 10:
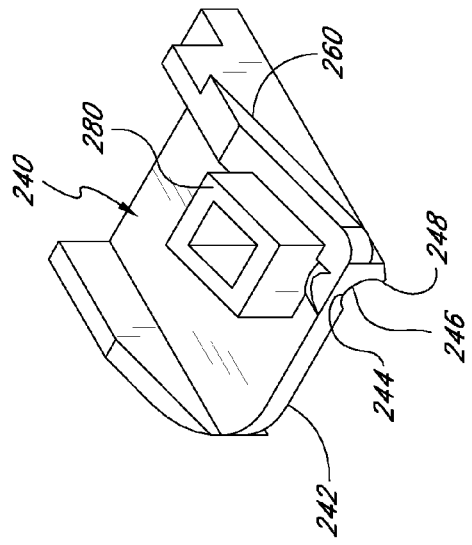
FIG. 10 is a second perspective view of the upper lens compactor of the apparatus of FIG. 3.
Figure 9:
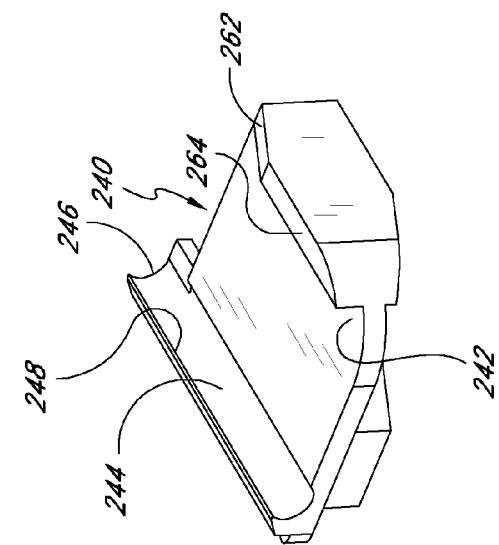
FIG. 9 is a perspective view of the upper lens compactor of the apparatus of FIG. 3.
Figure 20:
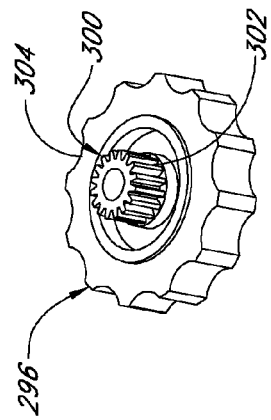
FIG. 20 is a lower perspective view of the pinion wheel of the apparatus of FIG. 3.
Figure 19:
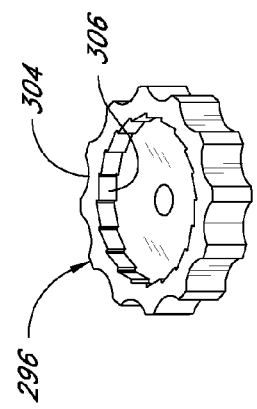
FIG. 19 is an upper perspective view of the pinion wheel of the apparatus of FIG. 3.
Figure 12:
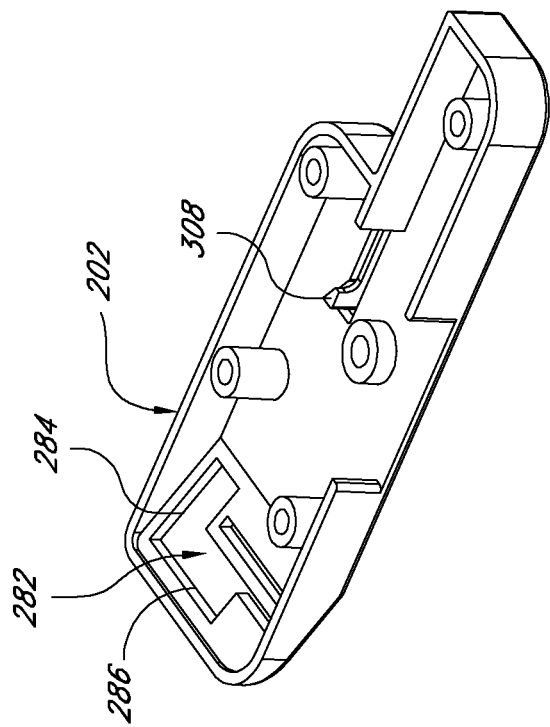
FIG. 12 is a second perspective view of the upper housing of the apparatus of FIG. 3.
Figure 11:
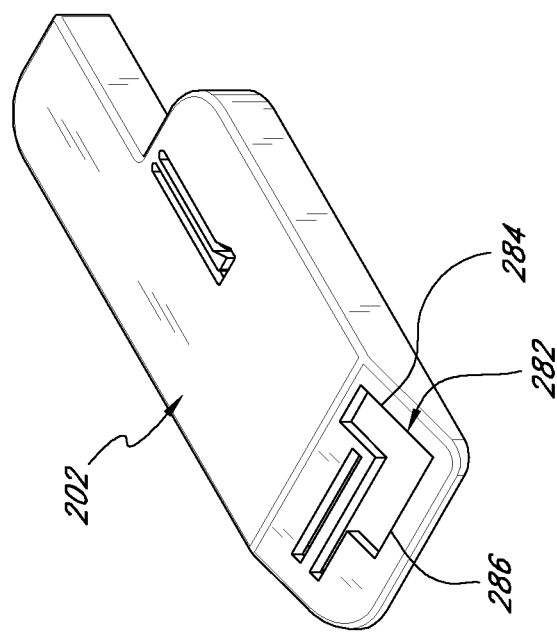
FIG. 11 is a perspective view of the upper housing of the apparatus of FIG. 3.
Figure 13:
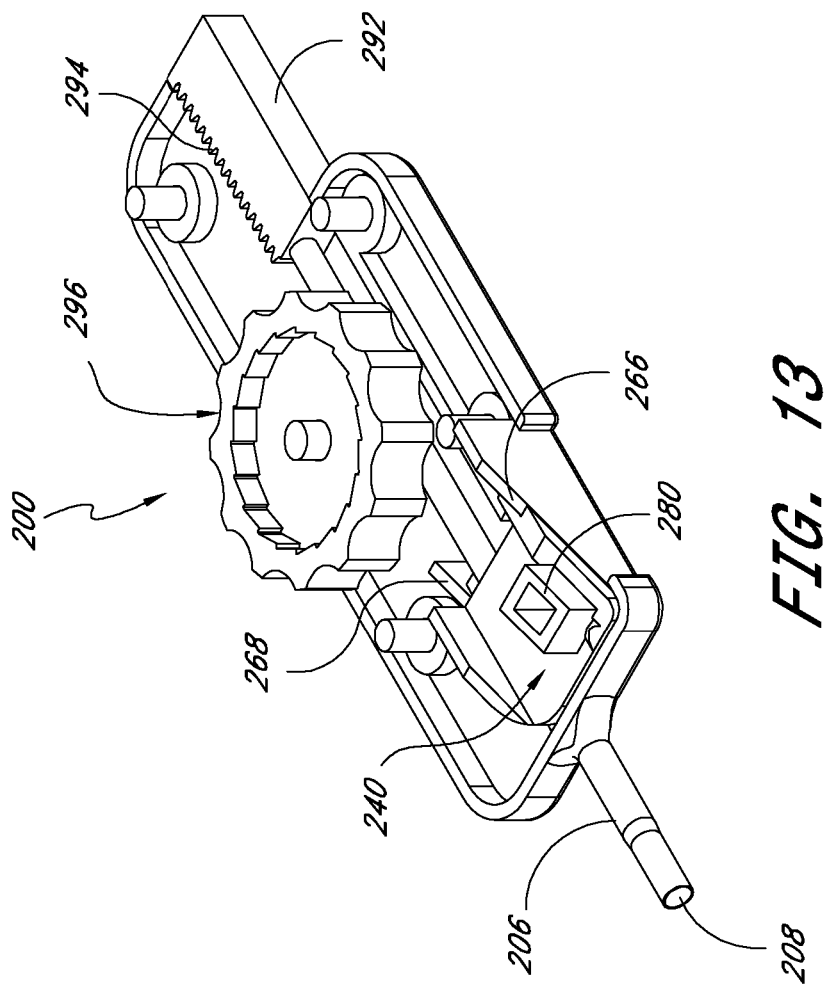
FIG. 13 is a perspective view of the apparatus of FIG. 3, with the upper housing portion removed for clarity, and the upper lens compactor moved to the first compacted position.

Referring again to FIGS. 3-5, and also to FIGS. 9-10, an upper lens compactor 240 is slidably disposed generally above the lower lens compactor 210. The lower and upper lens compactors 210, 240 together form a lens compactor of the apparatus 200. The depicted embodiment of the upper lens compactor 240 forms an upper engagement face 242 which preferably comprises a generally flat surface which, when the upper lens compactor is in position on the lower housing 204, defines a plane extending generally parallel to the delivery axis A-A. The upper lens compactor 240 preferably further comprises an upper insertion channel 244, which is preferably a partial cylinder in shape, with an inner surface 246 which extends from the upper engagement face 242 to an upper channel edge 248 which preferably extends generally parallel to the delivery axis A-A. (Alternatively, the insertion channels 214, 244 may taper inward as they extend forward, thereby forming a truncated cone or another inward-tapering surface upon their convergence when the upper lens compactor 240 is in the second compacted position (see below). Instead of or in addition to such a configuration of the insertion channels 214, 244, the inner surface of the delivery lumen 208 may also taper inward as it extends forward.)

In yet another embodiment, the delivery lumen 208 can have a generally oval cross-section (taken orthogonal to the delivery axis), with the channels 214, 244 shaped to have a similarly oval cross-section upon their convergence when the upper lens compactor 240 is in the second compacted position (see below).

The upper lens compactor 240 preferably further comprises first and second upper bearing surfaces 260, 262 disposed on respective opposite sides of the upper engagement face 242 and upper insertion channel 244, as well as a third upper bearing surface 264, which extends forward from the second upper bearing surface 262. The first, second and third upper bearing surfaces 260, 262, 264 preferably comprise generally flat surfaces which extend longitudinally, the first and second upper bearing surfaces 260, 262 being sloped with respect to the upper engagement face 242 and/or delivery axis A-A. The first and second upper bearing surfaces 260, 262 are (at least initially) slidably disposed against similarly-sloped first and second lower bearing surfaces 266, 268 formed on support ribs 270, 272 of the lower housing 204.

With reference now to FIGS. 3-5 and 9-12, the upper lens compactor 240 preferably also forms a compactor actuator 280 which, in the depicted embodiment, comprises a generally vertically-extending member suitable for manipulation by the thumb of a user. The compactor actuator 280 is received in a compactor guide 282 formed in the upper housing 202. In the depicted embodiment, the compactor guide 282 comprises a longitudinal slot 284 and a lateral slot 286 which are joined in an "L" configuration.

The upper and lower bearing surfaces 262, 264, 266, 268, and the compactor actuator 280 and compactor guide 282, coact to permit the upper lens compactor 240 to advance forward and downward from a home position (see FIGS. 3, 4, 15) in which the compactor actuator 280 is rearwardly disposed in the longitudinal slot 284, to a first compacted position (see FIGS. 13, 16) in which the compactor actuator 280 is forwardly disposed in the longitudinal slot 284, but has not yet been advanced laterally. This advancement of the upper lens compactor 240 moves the upper engagement face 242 forward and downward with respect to the lower engagement face 212, thereby reducing the vertical separation between the engagement faces 212, 242. The compactor actuator 280 and compactor guide 282 likewise coact to permit the upper lens compactor 240 to advance laterally from the first compacted position to a second compacted position (see FIGS. 14, 18) in which the compactor actuator 280 is laterally disposed in the lateral slot 286, remote from the longitudinal slot 284.

Figure 15:
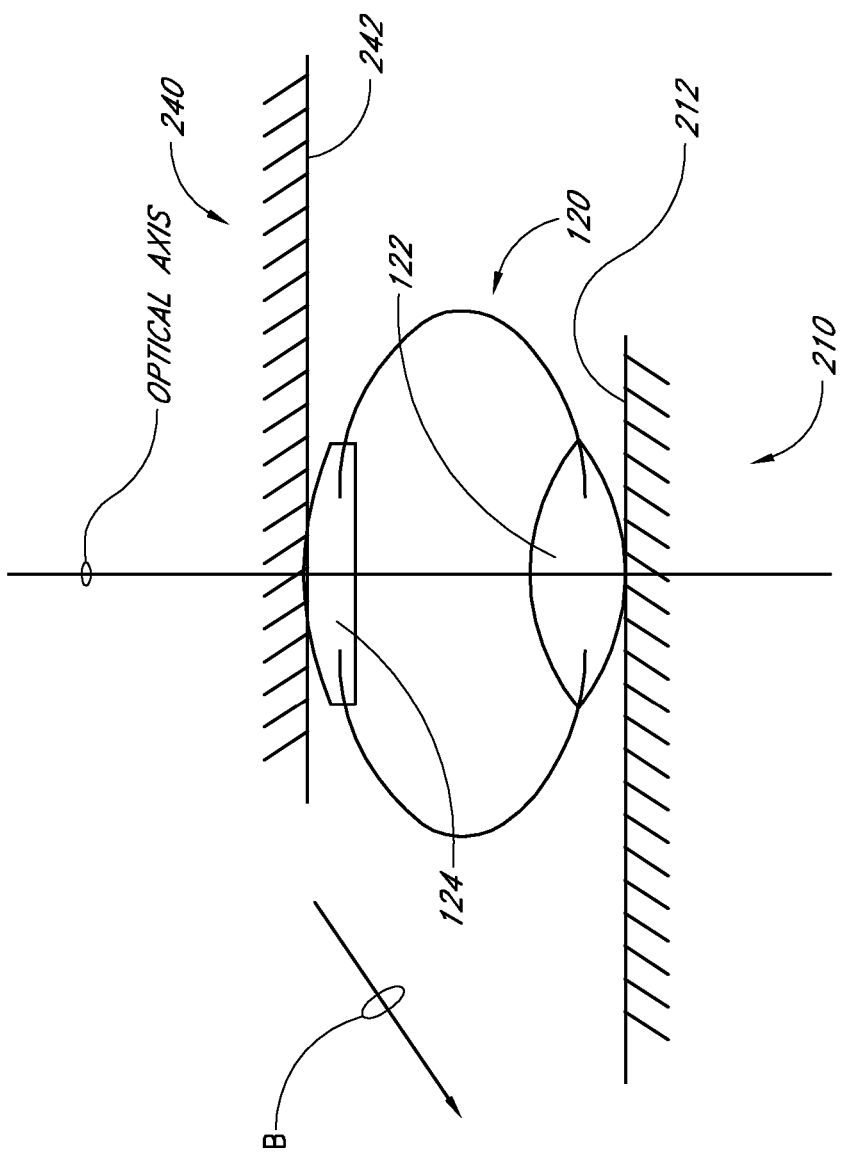
FIG. 15 is a schematic, side cross-sectional view of the apparatus of FIG. 3, with the upper lens compactor in the home position.

FIGS. 15-18 illustrate schematically the operation of the compactors 210, 240 in a circumstance in which a multiple-lens IOL, such as the IOL 120 described above, is stored or placed in the apparatus 200 for subsequent compaction and/or insertion. In FIG. 15, the upper lens compactor 240 is in the home position wherein the upper engagement face 242 is preferably generally parallel to the lower engagement face 212, and the multiple-lens IOL 120 is disposed between the faces 212, 242, preferably in a substantially unstressed condition in which the optical axes of the viewing elements are substantially coincident with each other, and/or with the optical axis of the IOL 120 itself.

Note that the IOL 120 is considered to be substantially unstressed even when the faces 212, 242 compress the viewing elements 122, 124 together somewhat, thereby slightly stressing the biasing members 126, 128. Accordingly, the separation between the faces 212, 242 may be chosen to slightly compress the viewing elements 122, 124 together when the upper lens compactor 240 is in the home position. The IOL 120 is also considered to be substantially unstressed when the faces 212, 242 draw the viewing elements 122, 124 apart somewhat, thereby slightly stressing the biasing members 126, 128. The separation between the faces 212, 242 may therefore be chosen to draw the viewing elements 122, 124 slightly apart when the upper lens compactor 240 is in the home position. The IOL 120 is also considered to be substantially unstressed when the outer faces or other portions of one or both of the viewing elements 122, 124 are deformed or stressed due to adhesion stresses between the faces 212, 242 and the viewing elements (which stresses can arise where the viewing elements 122, 124 comprise optics), as such stresses are relatively minor when viewed in the context of the entire IOL 120.

In the depicted embodiment, the engagement faces 212, 242 comprise generally flat surfaces constructed from a material to which the outer faces of the viewing elements 122, 124 will tend to self-adhere. For example, acetal (sold as DELRIN™) may be employed to construct one or both of the faces 212, 242; this material displays good adhesion properties with many of the materials (e.g., silicone, polyurethanes, hydrogels, acrylics, PVA, styrene-based copolymers) typically employed to construct IOLs. Of course, any other material having good adhesion properties with the contacted portions of the IOL may be employed to form the engagement faces 212, 242.

Figure 16:
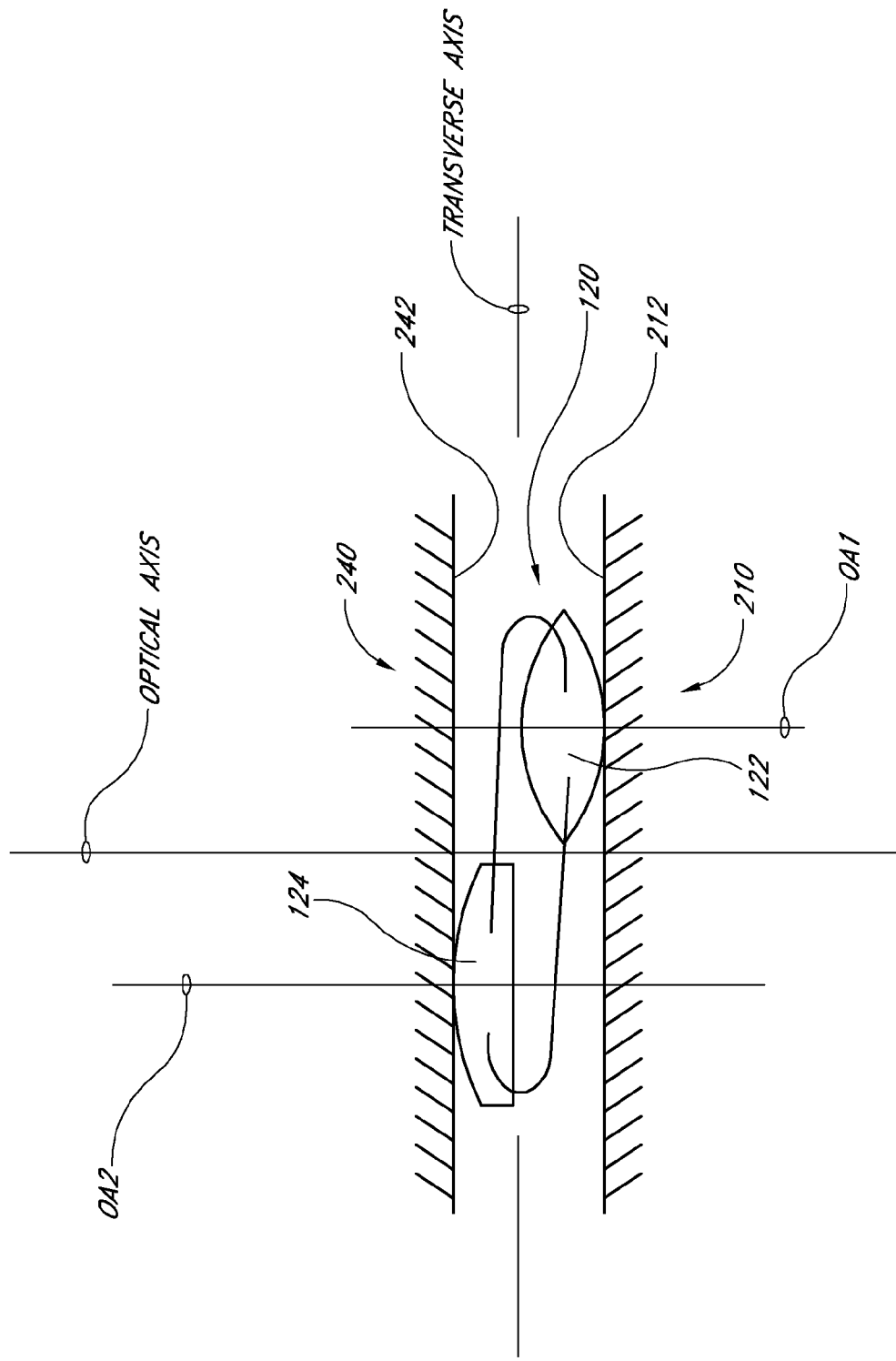
FIG. 16 is a schematic, side cross-sectional view of the apparatus of FIG. 3, with the upper lens compactor in the first compacted position.
Figure 17:
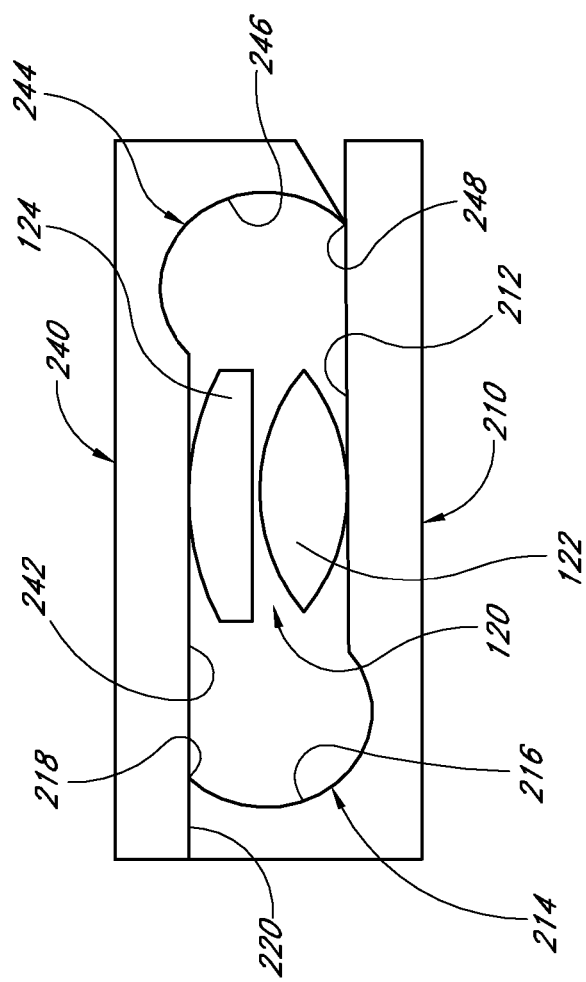
FIG. 17 is a schematic, front cross-sectional view of the apparatus of FIG. 3, with the upper lens compactor in the first compacted position.

From the home position depicted in FIG. 15, the upper engagement face 242 advances forward and downward, as indicated by the arrow B, to the first compacted position shown in FIGS. 16-17. With the upper engagement face in the first compacted position, the IOL 120 assumes a first compacted condition (also shown in FIGS. 16-17) in which the viewing elements 122, 124 are relatively displaced so that they are non-coaxial. (In other words, the optical axes OA1, OA2 of the individual viewing elements are non-coincident with each other, and/or with the optical axis of the IOL 120 itself.) In the depicted embodiment, the viewing elements 122, 124 are sufficiently relatively displaced when in the first compacted condition that no portion of the first viewing element 122 overlaps any portion of the second viewing element 124. However, in other embodiments the viewing elements 122, 124 may overlap somewhat (while being nonetheless non-coaxial), as the IOL 120 is viewed along the optical axis, while the IOL 120 is in the first compacted condition. Likewise, in the depicted embodiment no portion of the first viewing element 122 overlaps any portion of the second viewing element 124, as the IOL 120 is viewed along the transverse axis, when the IOL 120 is in the first compacted condition. However, in other embodiments the viewing elements 122, 124 may be sufficiently relatively displaced that they overlap somewhat, as the IOL 120 is viewed along the transverse axis, while the IOL 120 is in the first compacted condition. In still another embodiment, the IOL 120 may have an overall height, as measured along the optical axis, no greater than that of the higher of the first and second viewing elements 122, 124, when the IOL is in the first compacted condition. In the embodiment depicted in FIGS. 16-17, the height of the IOL 120, as measured along the optical axis, is substantially equal to the sum of the heights of the first and second viewing elements 122, 124.

As best seen in FIG. 17, when the upper lens compactor 240 is in the first compacted position, the upper channel edge 248 preferably contacts the lower engagement face 212 and the lower channel edge 218 preferably contacts the upper engagement face 242. In certain embodiments, the lower support surface 220 may also contact the upper engagement face 242. If desired, the IOL 120 may be lubricated when in the first compacted condition, using any suitable lubricant. The lubricant may assist in further compaction of the IOL 120.

Figure 14:
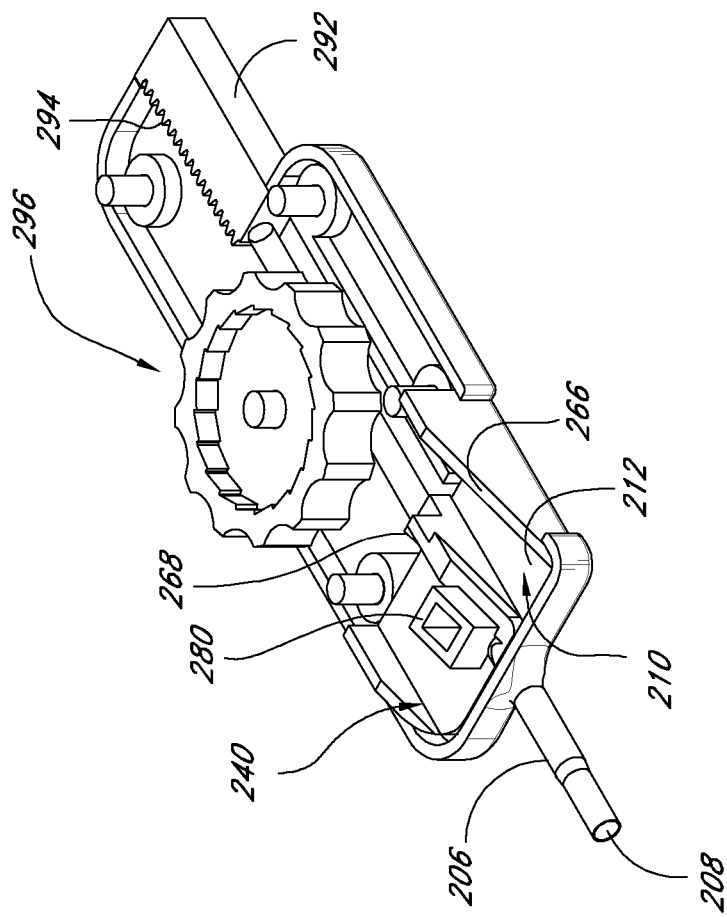
FIG. 14 is a perspective view of the apparatus of FIG. 3, with the upper housing portion removed for clarity, and the upper lens compactor moved to the second compacted position.
Figure 18:
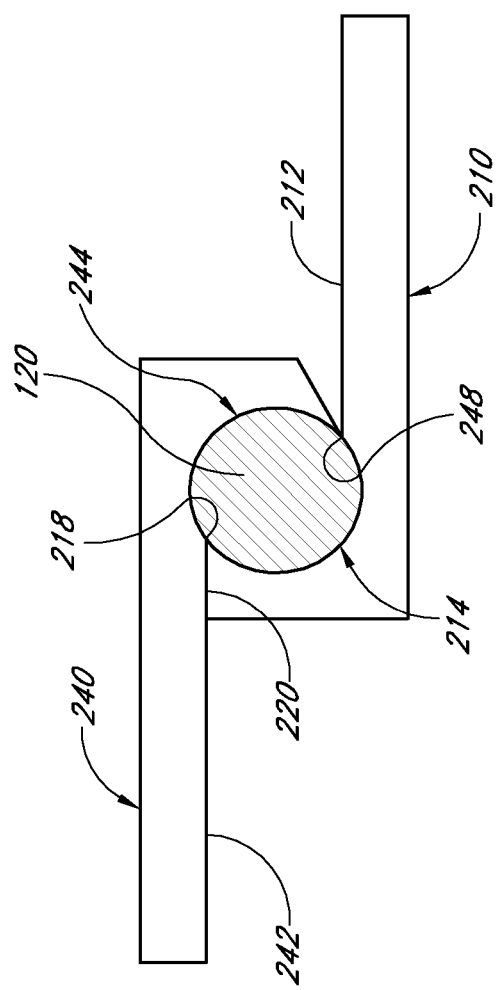
FIG. 18 a schematic, front cross-sectional view of the apparatus of FIG. 3, with the upper lens compactor in the second compacted position.

From the first compacted position, the upper lens compactor 240 may be advanced laterally to the second compacted position (see FIGS. 14, 18). As the upper lens compactor 240 is so advanced, the upper engagement face 242, inner surface 246 and/or upper insertion channel 244 urge the IOL 120 generally laterally toward the inner surface 216 and lower insertion channel 214. As best seen in FIG. 18, when the upper lens compactor 240 is in the second compacted position the upper insertion channel 244 is preferably disposed adjacent the lower insertion channel 214 such that they form a substantially complete cylinder which is substantially centered on the delivery axis A-A and forms a rearward extension of the delivery lumen 208. Accordingly, the inner surfaces 216, 246 and insertion channels 214, 244 "crush" the IOL 120 into a second compacted condition shown in FIG. 18.

With further reference to FIGS. 3-5 and 9-10, the apparatus 200 preferably further comprises a generally cylindrical driving member 290 which is disposed along the delivery axis A-A. (Where the delivery lumen 208 has an oval cross-section, the driving member 290 may have a similarly oval cross-section.) The rearward end of the driving member 290 is connected to a rack 292 which forms rack teeth 294 on one side thereof. A pinion wheel 296 is rotatably mounted on a pinion wheel bearing 298 which projects upward from the lower housing 204. The pinion wheel 296, shown in further detail in FIGS. 19-20, forms on its underside a pinion gear 300 comprising pinion teeth 302 which are configured to mesh with the rack teeth 294, upon manual advancement of the rack 292 and driving member 290 forward from a storage position (shown in FIGS. 4, 13-14) to a ready position (not shown) in which the forwardmost rack teeth 294 engage the pinion teeth 302. Once the rack 294 and driving member 290 reach the ready position, the user may manipulate the pinion wheel 296 via knurling 304 formed on the outer surface thereof, to advance the rack 294 and driving member longitudinally forward in the apparatus 200. As this is done, ratchet cogs 306 formed on an inner surface of the pinion wheel 296 cooperate with a ratchet pawl 308 formed on the upper housing 202 to prevent counter-rotation of the pinion wheel 296 or rearward motion of the rack 294 and driving member 290.

Where the IOL 120 has been compacted into the second compacted configuration (or is otherwise disposed in the lower insertion channel 214 or between the insertion channels 214, 244 when the upper lens compactor 240 is in the second compacted position), this forward movement of the driving member 290 causes the forward end of the driving member to advance through the lower insertion channel (or between the insertion channels 214, 244 when the upper lens compactor 240 is in the second compacted position), thereby urging the IOL 120 forward and into the delivery lumen 208 of the delivery probe 206. Further advancement of the driving member will then extrude the IOL from the forward end of the delivery probe 206.

Except where otherwise noted, the components of the apparatus 200 may be formed from any suitably rigid material, including plastics such as ABS. The lower housing 204 (or, alternatively, at least the lower lens compactor 210 and/or delivery probe 206) may be formed from a transparent plastic such as clear polycarbonate, to promote visibility of the IOL during compaction/delivery.

Accordingly, the apparatus 200 may be employed to deliver or insert an IOL, such as the IOL 120, into an eye, such as a human eye. In doing so, the user/physician first accesses an insertion location (e.g., the capsular bag, anterior chamber, etc) within the eye via any suitable technique, for example, by making a small incision or series of small incisions in the anterior structures of the eye. If necessary, the natural crystalline lens is removed via a suitable technique such as phacoemulsification. Through the incision(s) the physician inserts the forward end of the delivery probe 206, preferably after compacting the IOL as detailed above and, if desired, after advancing the IOL partway through the lumen 208 of the delivery probe 206. With the end of the delivery probe in place, the physician extrudes the IOL from the probe 206, thereby inserting the IOL in the eye. (By employing the apparatus 200, the compacting and delivery may be done without opening the housing 202/204 or otherwise manually accessing the IOL.) Upon departure from the probe 206, the IOL "un-compacts" by virtue of its elasticity, returning substantially to its unstressed condition. The physician then withdraws the probe 206 and, if necessary, adjusts the positioning of the IOL within the eye. Upon satisfactory positioning of the IOL, the physician closes the incision(s) to complete the operation.

FIGS. 21-29 depict another embodiment of an apparatus 400 for compacting and/or inserting an intraocular lens. In one embodiment, the apparatus 400 is generally similar to the apparatus 200 described above and depicted in FIGS. 3-20, except as further detailed below. Except where otherwise noted, the components of the apparatus 400 may be formed from any suitably rigid material, including plastics such as ABS.

The apparatus 400 preferably comprises an upper housing 402 and a lower housing 404 which cooperate to enclose and support the components of the apparatus 400. Disposed within the lower housing 404 is an injector plate 405 which forms a delivery probe 406 which in turn defines a delivery lumen 408; both the delivery probe 406 and lumen 408 extend along a longitudinally-oriented delivery or injection axis A-A of the apparatus 400. The injector plate 405 also forms a lower lens compactor or lower compacting element 410 comprising a lower engagement face or wall 412 and a lower insertion channel 414 which extends along the delivery axis A-A.

Figure 24:
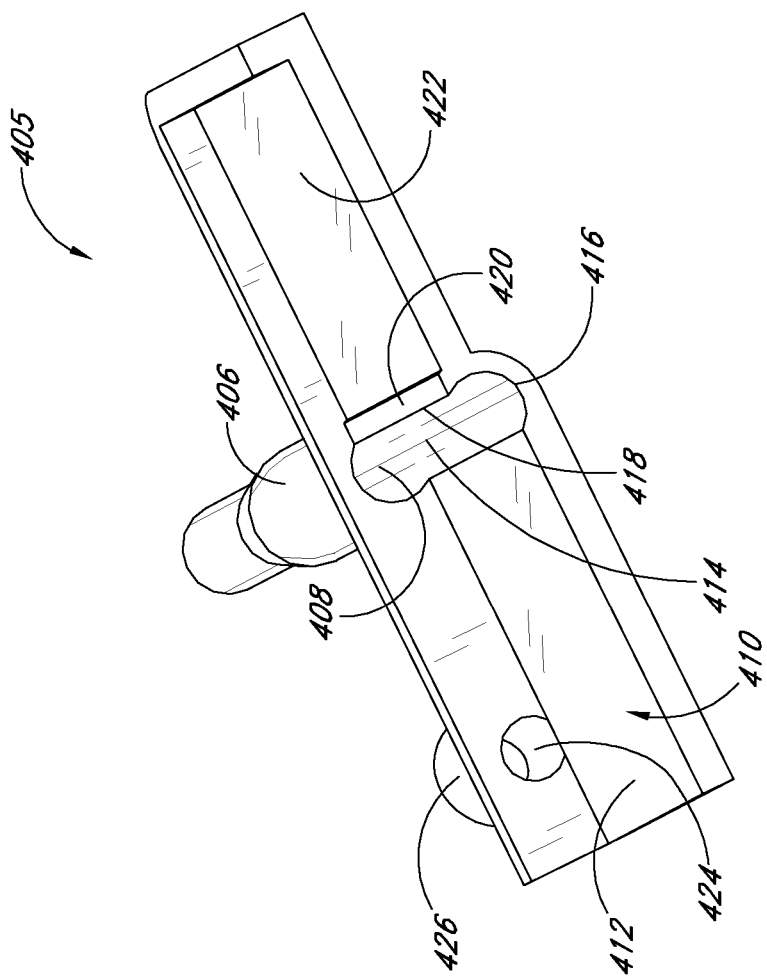
FIG. 24 is a perspective view of the injector plate of the apparatus of FIG. 21.

Best seen in FIG. 24, the lower engagement face 412 preferably comprises a generally flat surface which defines a plane extending generally parallel to (or intercepting) the delivery axis A-A. The lower insertion channel 414 is preferably a partial cylinder in shape, with an inner surface 416 which extends from the lower engagement face 412 to a lower channel edge 418 which preferably extends generally parallel to the delivery axis A-A. The lower insertion channel 414 preferably comprises a partial rearward extension, along the delivery axis A-A, of the inner surface of the delivery lumen 408. From the lower channel edge 418 a lower support surface 420 extends in a direction opposite the lower engagement face 412, while forming a generally flat surface which defines a plane extending generally parallel to the face 412. In the depicted embodiment, the lower support surface is slightly elevated with respect to a lower lateral surface 422 extending from the lower support surface 420 opposite the lower insertion channel 414. If desired, a lubricant opening 424 and lubricant fitting 426 may be provided in fluid communication with the lower lens compactor 410 to facilitate lubrication of the IOL during compaction.

The opening 424 also facilitates visibility of the IOL within the apparatus 400 at various stages of the compaction/delivery process. To further promote visibility of the IOL during compaction/delivery, a window or opening 407 may be formed in the lower housing 404 (see FIGS. 21-22, 28), and the lower engagement face 412 (or the entire injector plate 405) may be formed from a transparent material. Where the entire injector plate 405 is constructed from a transparent material, the post-compaction condition of the IOL will be visible in the delivery probe 406.

Figure 25:
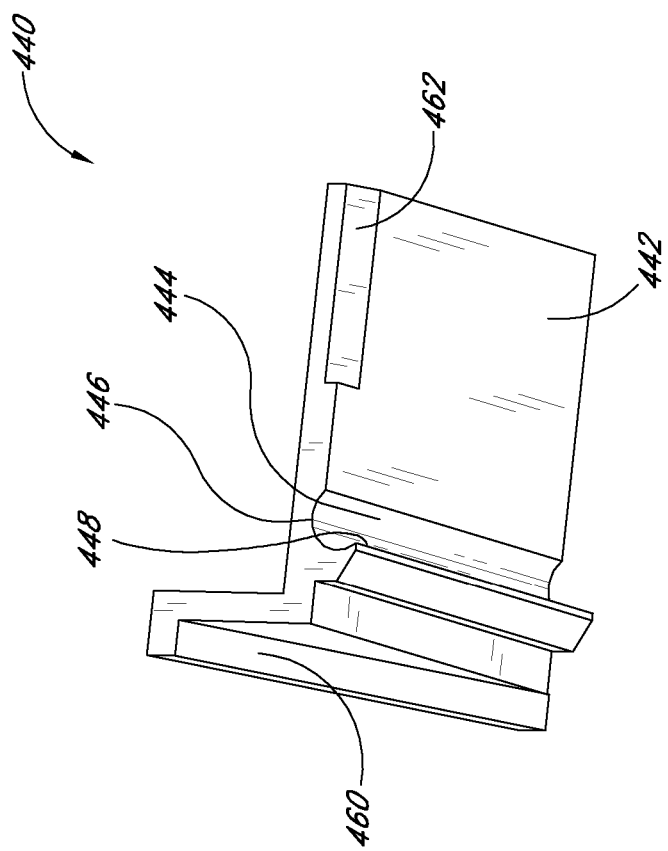
FIG. 25 is a perspective view of the upper lens compactor of the apparatus of FIG. 21.
Figure 26:
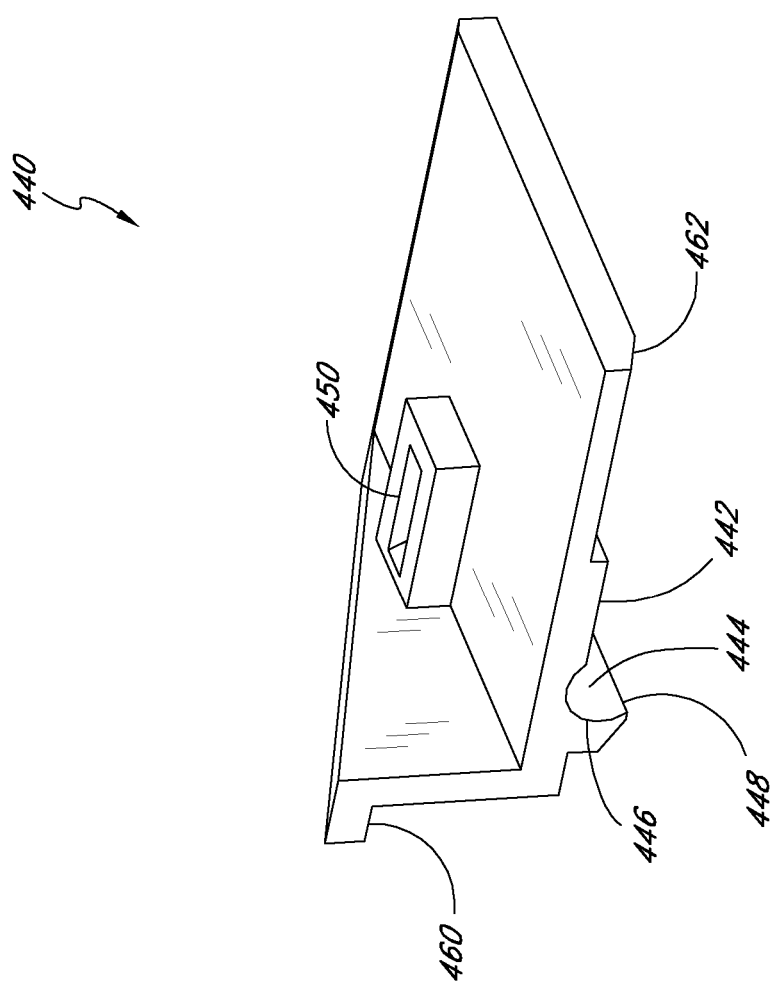
FIG. 26 is a second perspective view of the upper lens compactor of the apparatus of FIG. 21.

Referring again to FIGS. 21-22 and also to FIGS. 25-26, an upper lens compactor 440 is slidably disposed generally above the lower lens compactor 410. The lower and upper lens compactors 410, 440 together form a lens compactor of the apparatus 400. The upper lens compactor 440 forms an upper engagement face 442 which preferably comprises a generally flat surface which, when the upper lens compactor is in position on the lower housing 404, defines a plane extending generally parallel to the delivery axis A-A. The upper lens compactor 440 preferably further comprises an upper insertion channel 444, which is preferably a partial cylinder in shape, with an inner surface 446 which extends from the upper engagement face 442 to an upper channel edge 448 which preferably extends generally parallel to the delivery axis A-A. (Alternatively, the insertion channels 414, 444 may taper inward as they extend forward, thereby forming a truncated cone or another inward-tapering surface upon their convergence when the upper lens compactor 440 is in the second compacted position (see below). Instead of or in addition to such a configuration of the insertion channels 414, 444, the inner surface of the delivery lumen 408 may also taper inward as it extends forward.)

In yet another embodiment, the delivery lumen 408 can have a generally oval cross-section (taken orthogonal to the delivery axis), with the channels 414, 444 shaped to have a similarly oval cross-section upon their convergence when the upper lens compactor 440 is in the second compacted position (see below).

The upper lens compactor 440 preferably further comprises first and second upper bearing surfaces 460, 462 disposed on respective opposite sides of the upper engagement face 442 and upper insertion channel 444. The first and second upper bearing surfaces 460, 462 preferably comprise generally flat surfaces which extend longitudinally and are sloped with respect to the upper engagement face 442 and/or delivery axis A-A. The first and second upper bearing surfaces 460, 462 are (at least initially) slidably disposed against similarly-sloped first and second lower bearing surfaces 466, 468 formed on support ribs 470, 472 of the lower housing 404 (see FIG. 29). The upper lens compactor 440 further comprises an interface slot 450 which mates with an interface tab 452 formed on a compactor actuator 480.

Figure 27:
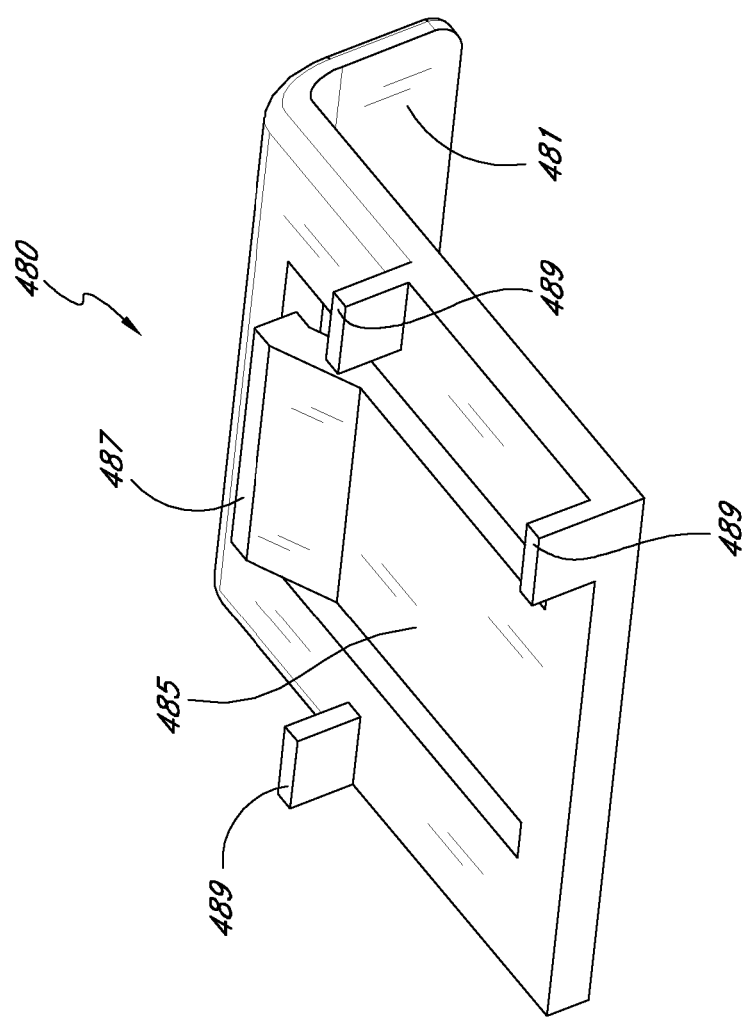
FIG. 27 is a perspective view of the compactor actuator of the apparatus of FIG. 21.
Figure 28:
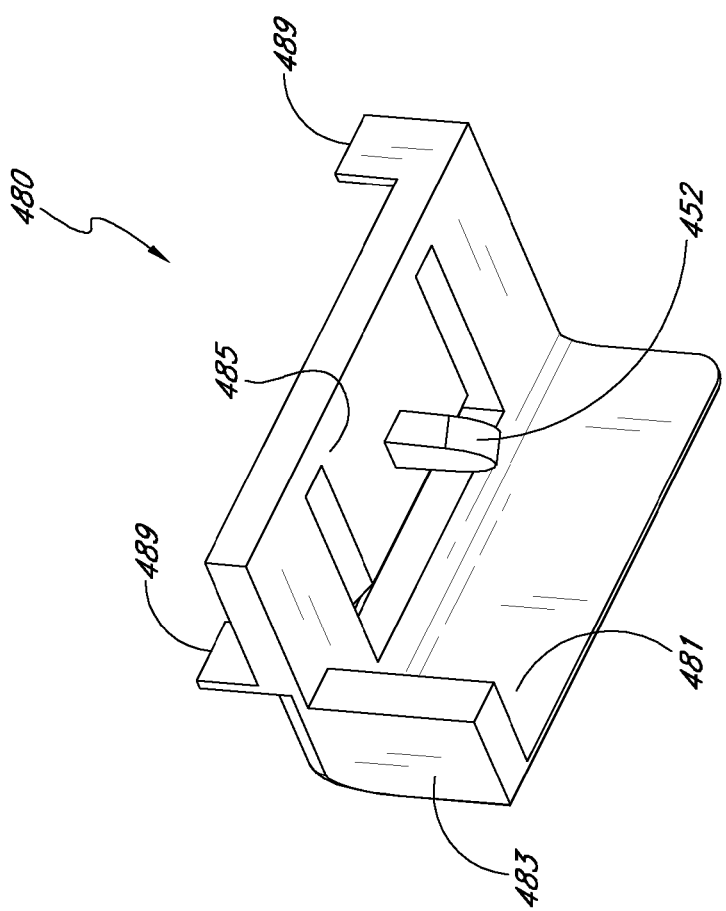
FIG. 28 is a second perspective view of the compactor actuator of the apparatus of FIG. 21.
Figure 29:
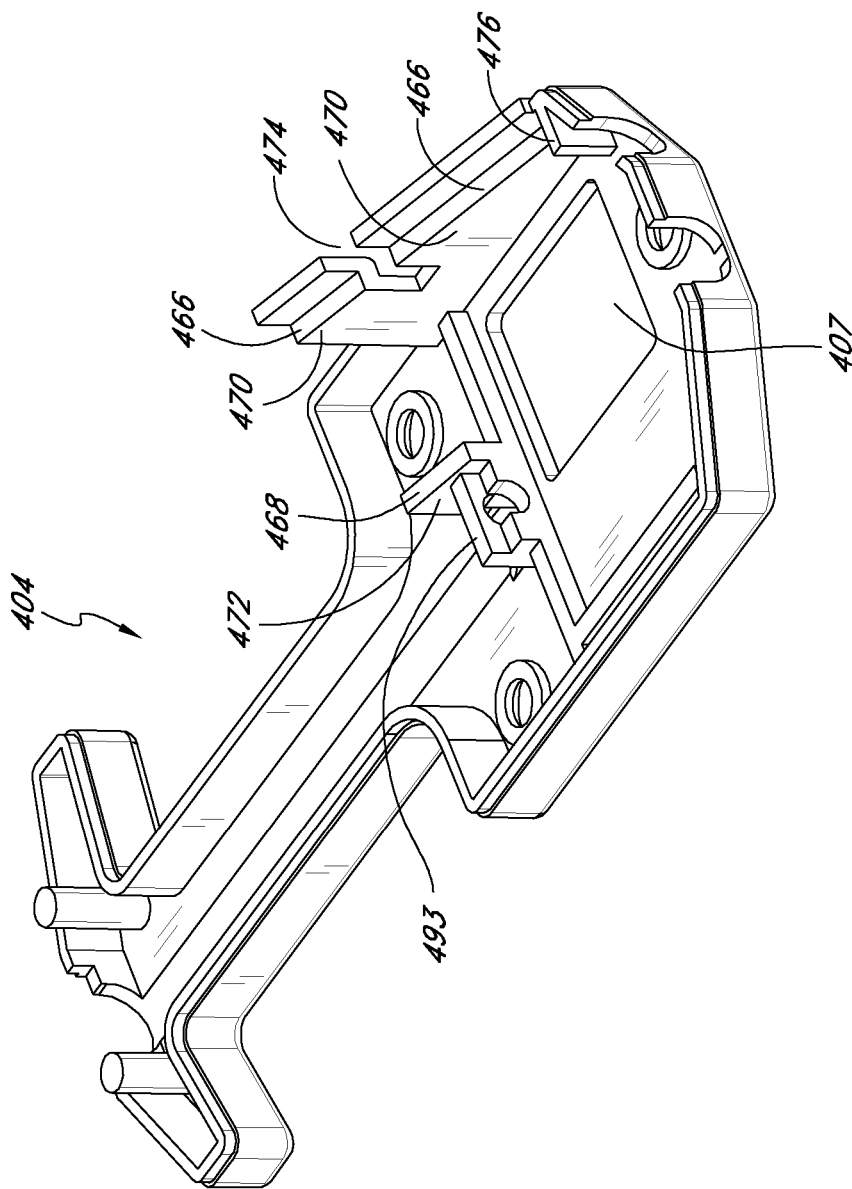
FIG. 29 is a perspective view of the lower housing of the apparatus of FIG. 21.

FIGS. 27-28 depict a preferred configuration of the compactor actuator 480. The actuator 480 preferably comprises a unitary member having a generally longitudinal handle 481 and a generally lateral guide rib 483. A spring member 485 extends laterally across an opening formed in the upper surface of the compactor actuator 480, and forms a spring tab 487 on its free end. Extending generally upward from the upper surface of the compactor actuator 480 are a number of guide projections 489, the upper ends of which are disposed within corresponding compactor guides 482 (see FIG. 22) formed on the inward upper surface of the upper housing 402. In the depicted embodiment, each of the compactor guides 482 comprises a generally longitudinal slot 484 and a generally lateral slot 486 which are joined in an "L" configuration. The lateral slot(s) 486 may extend purely laterally, or (in the depicted embodiment) they may be angled slightly forward, forming an angle of slightly more than 90 degrees with the corresponding longitudinal slot(s) 484.

Thus, the compactor actuator 480 is employed to move and guide the upper lens compactor 440 along a range of motion (similar to that of the upper lens compactor 240 of the apparatus 200) between a home position, first compacted position and second compacted position. At the home position, the upper lens compactor 440 is rearwardly disposed on the ribs 470, 472, with the first upper bearing surface 460 resting on the first lower bearing surface 466 and straddling a gap 474 formed in the surface 466/rib 470, and with the second upper bearing surface 462 resting on the second lower bearing surface 468. In one embodiment, the rearward edges of the surfaces 460 and 466 (and/or those of the surfaces 462 and 468) are aligned when the upper lens compactor 440 is in the home position.

From the home position, the actuator 480 and compactor 440 can be moved longitudinally forward by appropriate manipulation of the handle 481, to the first compacted position in which the first upper bearing surface 460 may remain on the first lower bearing surface 466, but forward of the gap 474, and the second upper bearing surface 462 is displaced forward of, and no longer rests on, the second lower bearing surface 468. In addition, the lateral guide rib 483 is longitudinally aligned with or forward of the gap 474, thereby permitting (subsequent) inward lateral movement of the actuator 480 and compactor 440, and the guide projections 489 are disposed at the forward ends of the longitudinal slots 484 of the corresponding compactor guides 482 (see FIG. 22). The first compacted position is, in one embodiment, further characterized by relative situation of the compactors 410, 440, bearing faces 412, 442, channels 414, 444, edges 418, 448, etc. in a manner similar to that depicted in FIGS. 16-17 with regard to the apparatus 200. In another embodiment, the first compacted position is still further characterized by contact between a forward edge of the upper lens compactor 440 and a stop member 476 formed on the lower housing 404.

From the first compacted position, the actuator 480 and compactor 440 can be moved generally laterally inward to the second compacted position. The second compacted position is, in one embodiment, characterized by relative situation of the compactors 410, 440, bearing faces 412, 442, channels 414, 444, edges 418, 448, etc. similar to that depicted in FIG. 18 with regard to the apparatus 200. As the compactor 440 and actuator 480 advance laterally inward, their motion is guided by the interaction of the guide projections 489 and the lateral slots 486 of the corresponding compactor guides 482, until the second compacted position is reached. In addition, the lateral guide rib 483 moves laterally into the housings 402, 404 through the gap 474. In one embodiment, the spring member 485 and spring tab 487 of the actuator 480 move sufficiently laterally inward to cause the outer edge of the tab 487 to engage the inner edge of a locking ridge 488 (see FIG. 22) formed on the upper housing 402. The spring member 485 prevents disengagement of the tab 487 and ridge 488, thereby preventing backward/outward lateral movement of the actuator 480 and upper lens compactor 440, once the second compacted position has been reached. This in turn ensures the creation of a rigid, stable "cylinder" at the meeting of the upper and lower insertion channels 414, 444 in the second compacted position, and a smooth longitudinal advancement of the compacted IOL from the "cylinder" into the delivery probe 406. Where employed, the spring member 485, tab 487 and ridge 488 also cooperate to make the apparatus 400 a single-use device, ensuring that factory-controlled standards for sterility, suitability of IOL type, etc. may be enforced with respect to each use of an apparatus 400.

Figure 21:
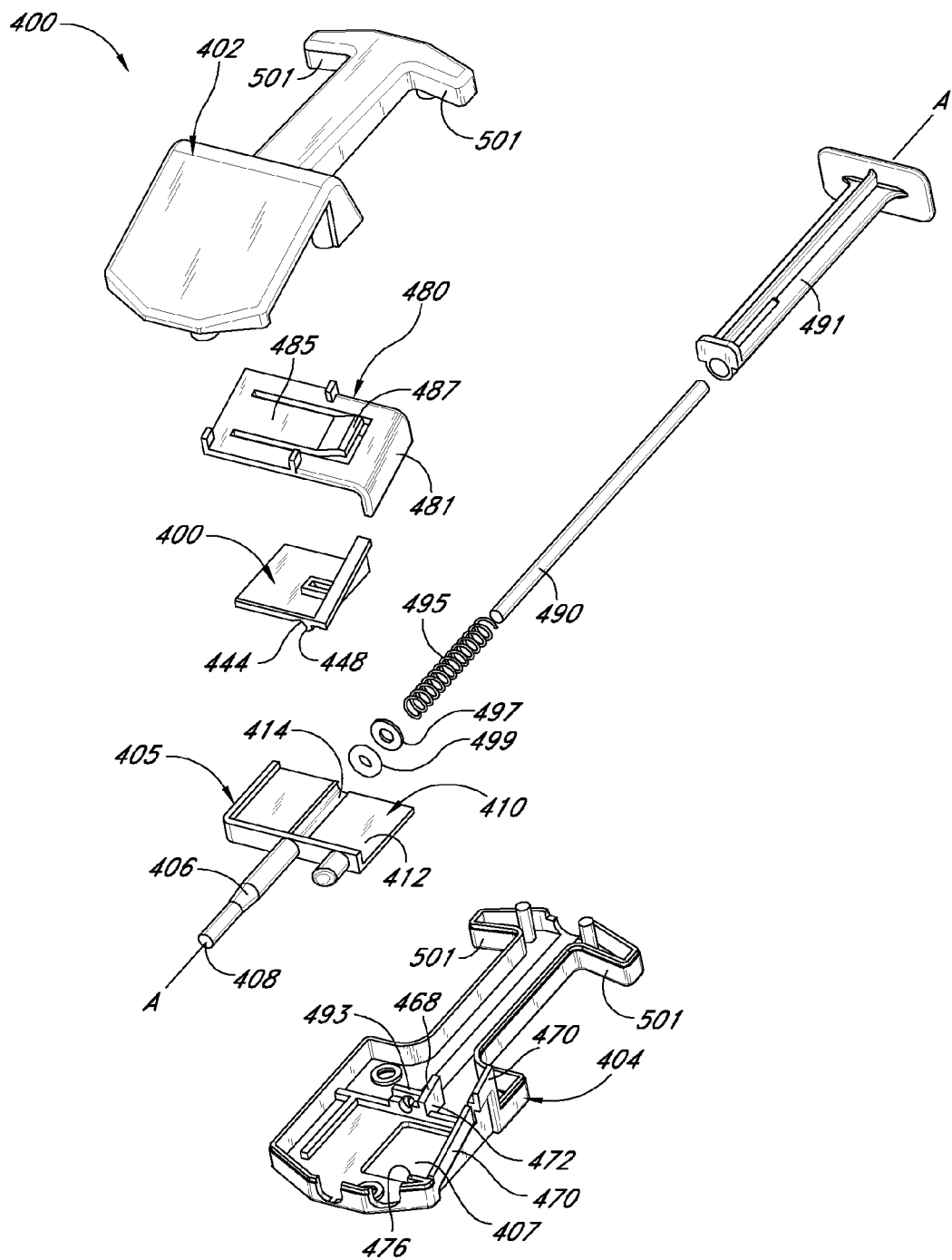
FIG. 21 is an exploded view of a second embodiment of an apparatus for compacting and/or inserting an intraocular lens.
Figure 22:
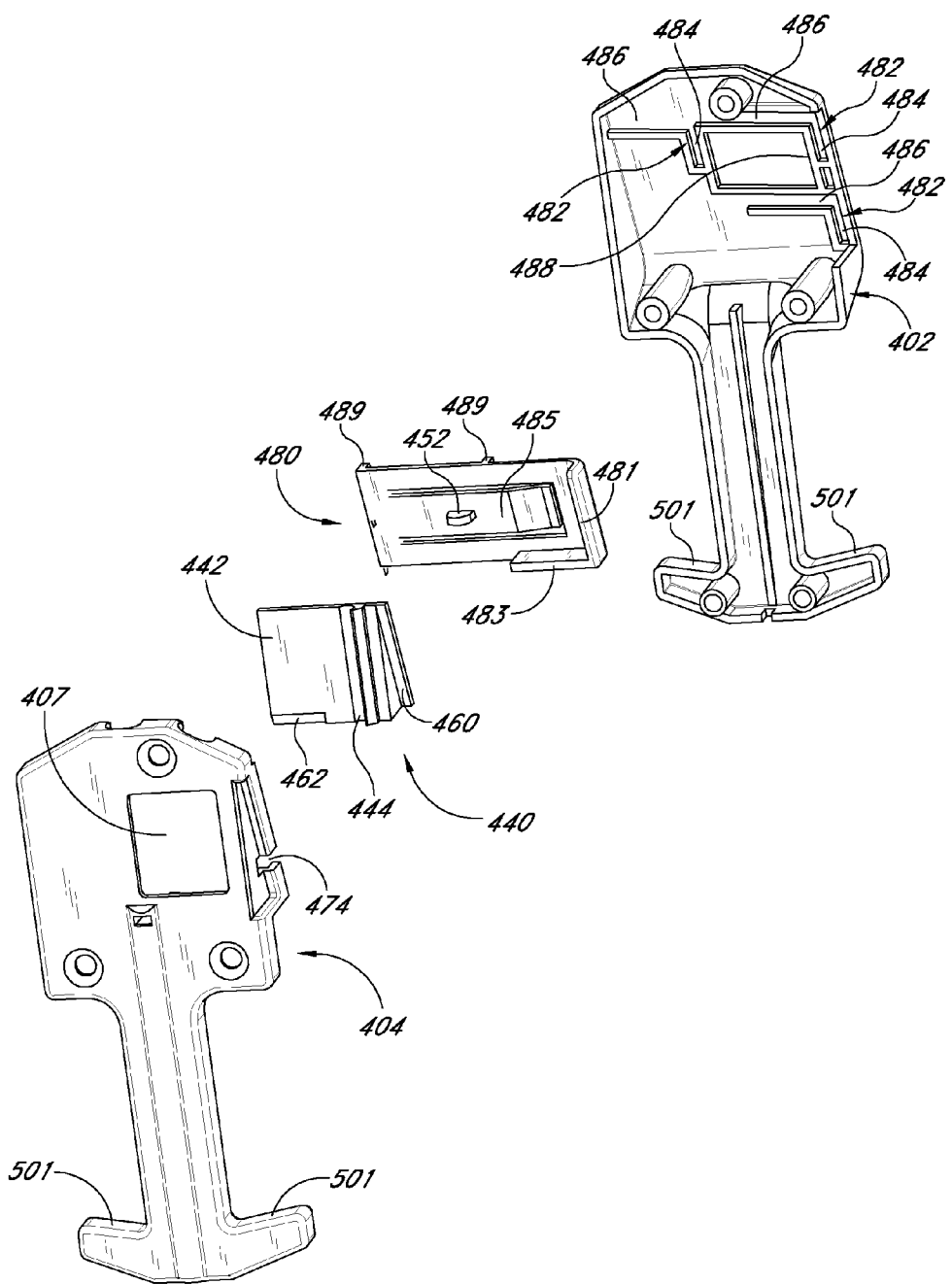
FIG. 22 is a second, partial exploded view of the apparatus of FIG. 21.
Figure 23:
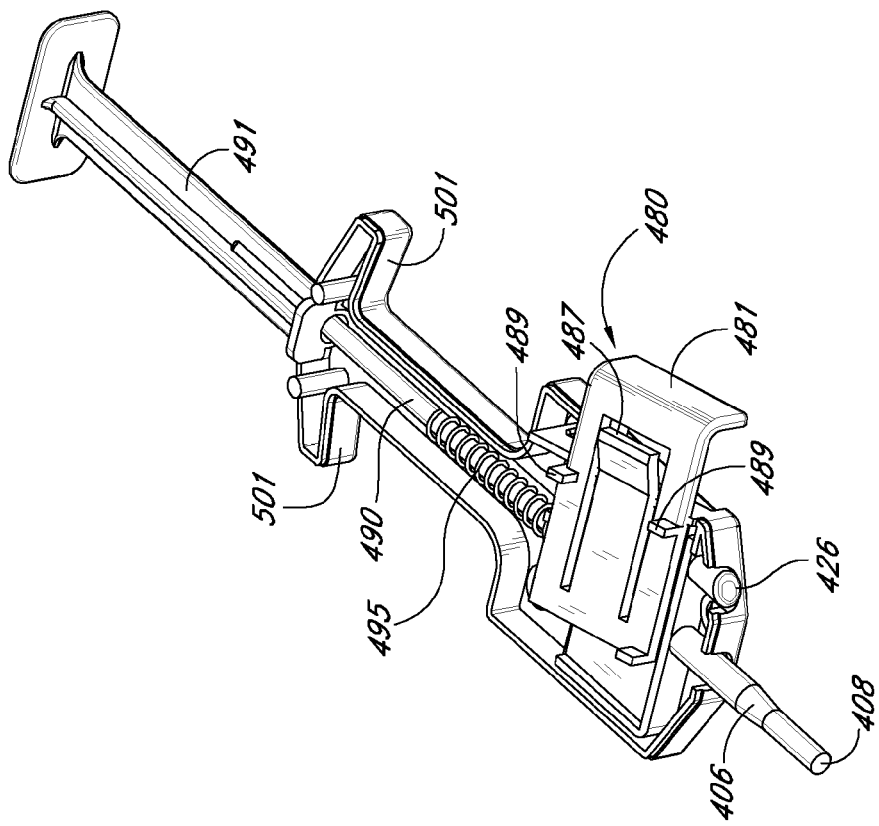
FIG. 23 is a perspective view of the apparatus of FIG. 21, with the upper housing removed for clarity.

With further reference to FIGS. 21-22, the apparatus 400 further comprises a generally cylindrical driving member 490 which is disposed along the delivery axis A-A. (Where the delivery lumen 408 has an oval cross-section, the driving member 490 may have a similarly oval cross-section.) The rearward end of the driving member 490 is received in a plunger 491 which is slidably disposed between the upper and lower housings 402, 404. The lower housing 404 forms a driving member guide 493 situated on the delivery axis A-A. Via appropriate manipulation of the plunger 491, the driving member 490 is longitudinally moveable from a retracted position (shown in FIG. 23), in which the forward end of the driving member 490 is situated in the driving member guide 493, forward through the lower insertion channel 414 (or between the insertion channels 414, 444 when the upper lens compactor 440 is in the second compacted position), thereby urging the IOL 120 forward and into the delivery lumen 408 of the delivery probe 406. Further advancement of the driving member will then extrude the IOL from the forward end of the delivery probe 406.

A spring 495, washer 497 and O-ring 499 may be situated surrounding the driving member 490 between the driving member guide 493 and the plunger 491. In addition, finger grips 501 may be provided on the upper and/or lower housings 402, 404 to facilitate holding the apparatus 400 between the thumb and forefingers, in a "syringe" fashion, with the thumb on the rear of the plunger 491 and one forefinger on each of the finger grips 501. This arrangement likewise facilitates single-handed operation of the apparatus 400 when delivering/inserting an IOL situated in the lower insertion channel 414. The spring 495 provides resistance and tactile feedback when a user is urging the driving member 490 forward with the plunger 491; if desired, the spring 495 and plunger 491 may be sized to reach an abutting relation (and thereby provide this resistance/feedback) once the forward end of the plunger 491 has entered the delivery lumen 408.

Accordingly, the apparatus 400 may be employed to deliver or insert an IOL, such as the IOL 120, into an eye, such as a human eye. In doing so, the user/physician first accesses an insertion location (e.g., the capsular bag, anterior chamber, etc) within the eye via any suitable technique, for example, by making a small incision or series of small incisions in the anterior structures of the eye. If necessary, the natural crystalline lens is removed via a suitable technique such as phacoemulsification. Through the incision(s) the physician inserts the forward end of the delivery probe 406, preferably after compacting the IOL as detailed above and, if desired, after advancing the IOL partway through the lumen 408 of the delivery probe 406. With the end of the delivery probe in place, the physician extrudes the IOL from the probe 406, thereby inserting the IOL in the eye. (By employing the apparatus 400, the compacting and delivery/insertion may be done without opening the housing 402/404 or otherwise manually accessing the IOL.) Upon departure from the probe 406, the IOL "un-compacts" by virtue of its elasticity, returning substantially to its unstressed condition. The physician then withdraws the probe 406 and, if necessary, adjusts the positioning of the IOL within the eye. Upon satisfactory positioning of the IOL, the physician closes the incision(s) to complete the operation.

Various embodiments of the apparatus 200/400 disclosed herein advantageously facilitate delivery of an IOL into the eye of a patient without need for a physician to handle the IOL or manually load it into an insertion device. For example, the IOL may be positioned within the lens compactor (e.g., between the upper and lower lens compactors) of the apparatus 200/400 during manufacture/assembly of the apparatus. The apparatus 200/400, with the IOL thus disposed inside the lens compactor, may then be sterilized as a unit, either at the point of manufacture or at some downstream location. Where appropriate, the sterilized apparatus-IOL assembly may be contained in a sterile package, wrapper, bag, envelope, etc. in which the apparatus-IOL assembly may remain until arrival at the point (or time) of use. (The apparatus-IOL assembly may be sterilized before and/or after placement in the package, etc.) This further facilitates a simple point-of-use procedure for medical personnel involved in implanting the IOL contained in the apparatus 200/400: after opening (any) packaging, the physician, or other medical personnel, can compact and insert the IOL using the apparatus 200/400 as discussed above, without (any need for) removing the IOL from the apparatus. Accordingly, there is no need to handle the IOL or manually load it into an insertion device at the point of use, both of which can be difficult and tedious, and can compromise the sterility of the IOL.

Figure 30:
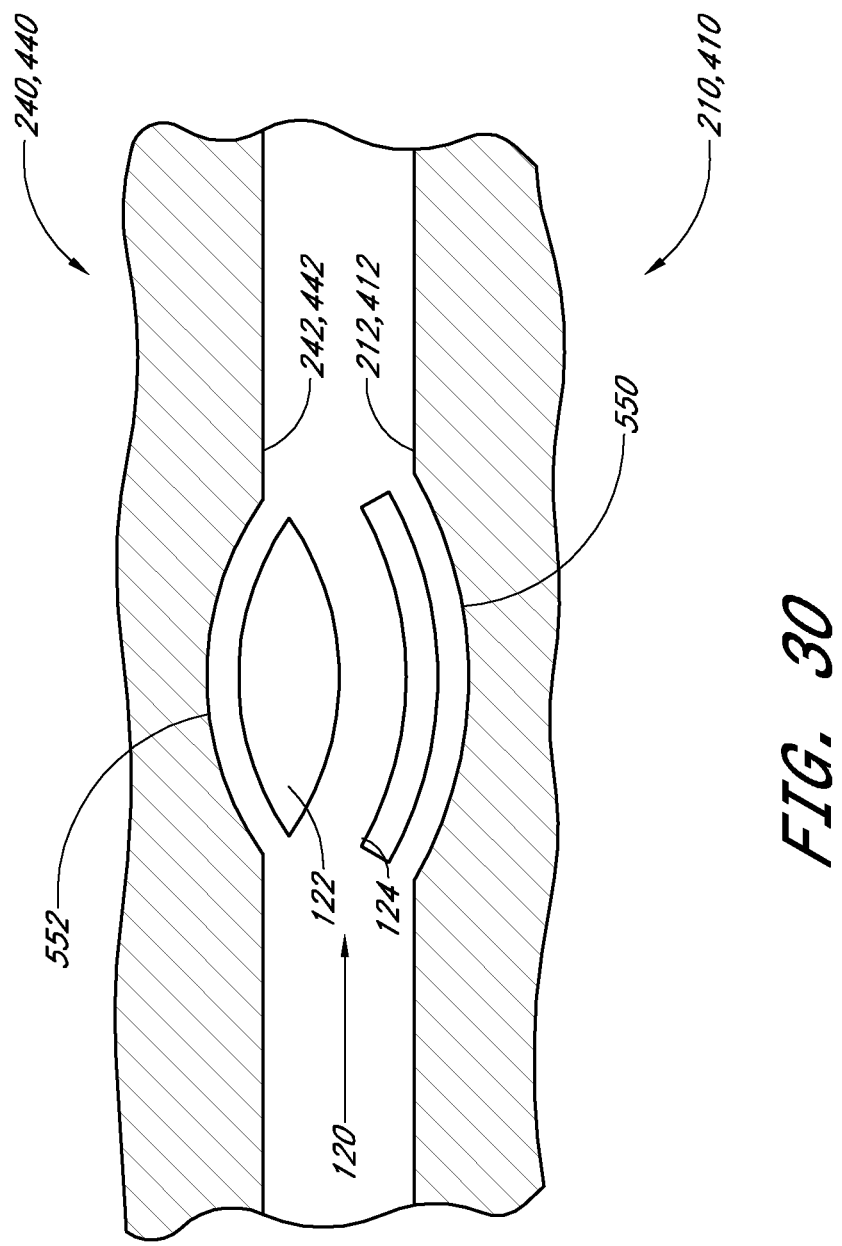
FIG. 30 is a schematic, cross-sectional view of alternative engagement faces for use with the disclosed apparatus.
Figure 31:
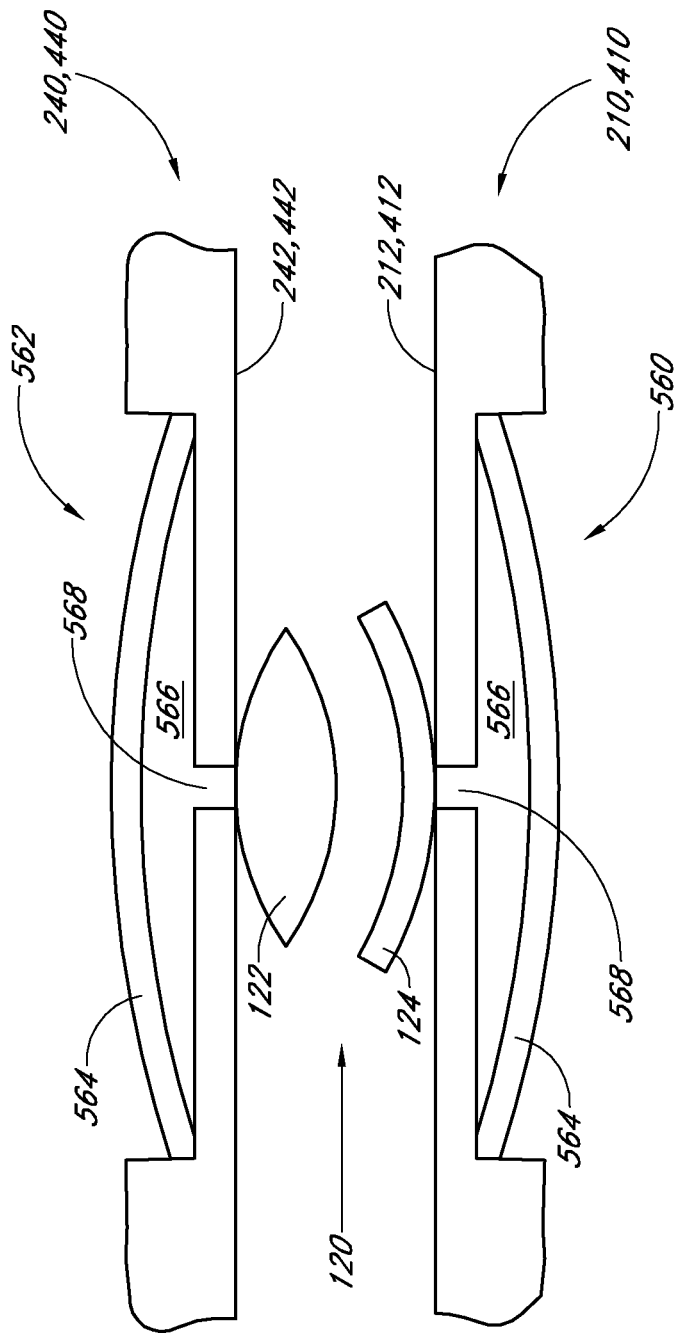
FIG. 31 is a schematic, cross-sectional view of vacuum-type engagement faces for use with the disclosed apparatus.
Figure 32:
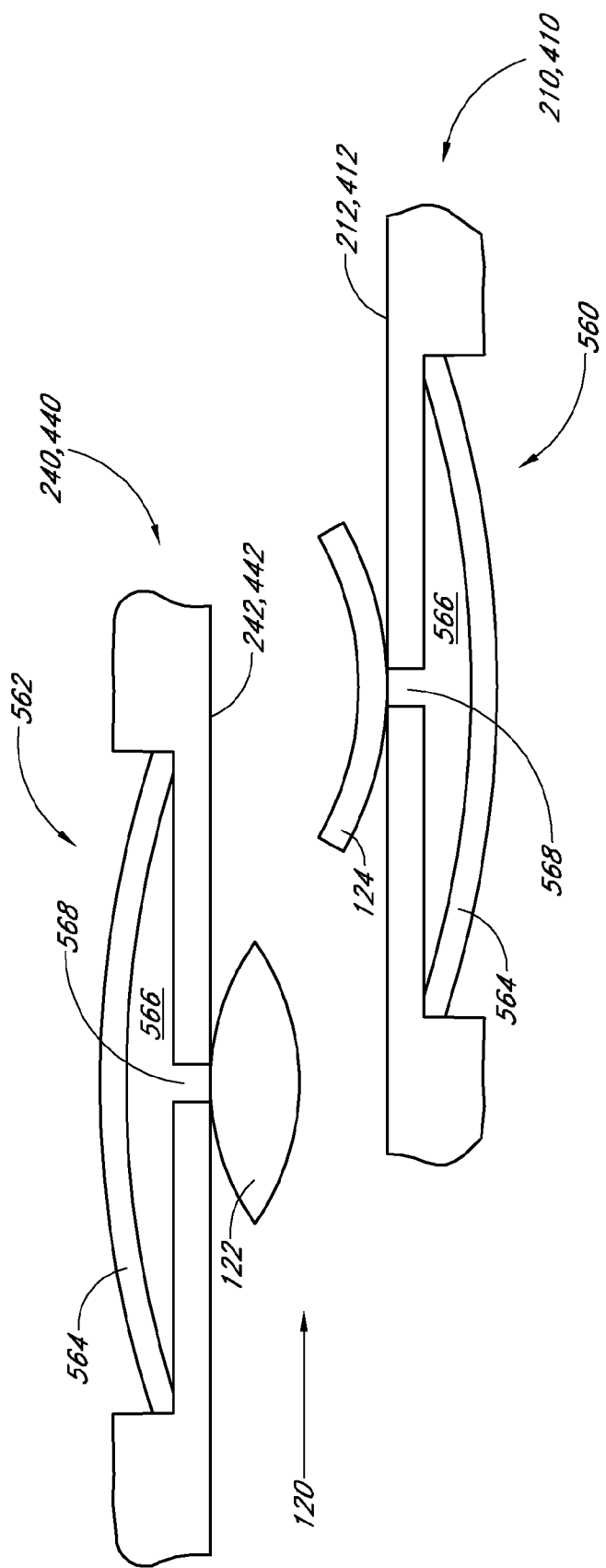
FIG. 32 is a schematic, cross-sectional view of vacuum-type engagement faces for use with the disclosed apparatus, with the upper lens compactor in the first compacted position.

FIGS. 30-32 depict alternative structures that may be employed in connection with one or both of the lower and upper engagement faces 212/412, 242/442, instead of or in addition to the generally flat surfaces described above. For example, FIG. 31 depicts the use of one or more pockets 550, 552 formed in the faces 212/412, 242/442. The pockets 550, 552 may be suitably shaped (e.g. as partial, substantially cylindrical or spherical shells, or with a rectangular or other polygonal profile) to grip the respective viewing elements 124, 122. In a further embodiment, the pocket(s) 550, 552 may be formed from a material, such as any of the materials discussed above, having an adhesive affinity for the material (s) employed to construct the outer faces of the viewing elements.

As seen in FIGS. 31-32, vacuum grips 560, 562 may be employed in connection with the engagement face(s) 212/412, 242/442. In the depicted embodiment, each vacuum grip 560, 562 comprises a domelike button 564 enclosing a vacuum chamber 566 in fluid communication with a relief opening 568 formed in the respective engagement face(s) 212/412, 242/442 which is positioned to abut the respective viewing element(s) 124, 122. Thus, depression of the button (s) 564 expels air from the relief openings 568, and the resilient properties of the button(s) 564 are sufficient to urge the button(s) 564 toward their original position. The negative pressure thereby created in the vacuum chamber(s) 566 draws the viewing element(s) 124, 122 against the engagement face (s) 212/412, 242/442. With the viewing elements so gripped, the compactors 210/410, 240/440 may be relatively moved to place the IOL 120 in the first compacted configuration shown in FIG. 32.

As yet another alternative, one or both of the engagement face 212/412, 242/442 may be suitably roughened to engage the viewing elements 122, 124. Such surface roughening may be employed on its own, or in connection with any of the alternatives discussed herein for constructing the engagement face 212/412, 242/442. In one embodiment, the surfaces in question are sanded; as one example, 100 grit sandpaper may be employed. In other embodiments, the surfaces may be ribbed, knurled, etc.

In further embodiments of the apparatus 200/400, the lower housing 204/404, lower lens compactor 210/410 and/or upper lens compactor 240/440 may be configured such that the upper lens compactor 210/410 is moveable only from the first compacted position to the second compacted position. In other words, the first compacted position replaces the home position as the "start" location of the upper lens compactor 240/440, which can move from the first compacted position to the second compacted position in the manner already described. Any or all of the structures described above as facilitating longitudinal movement of the upper lens compactor 210 between the home and first compacted positions may be omitted, if desired. The balance of the structure and function of the apparatus 200/400 preferably remains as described above.

Such a modified apparatus 200/400 is particularly useful for compacting and/or inserting a single-lens IOL, such as (but not limited to) the IOL 100 described above. Alternatively, a multiple-lens IOL, such as (but not limited to) the IOL 120 described above, may be compacted and/or inserted with this modified apparatus. In one embodiment, the multiple-lens IOL is disposed or stored in the compactor in the first compacted condition described above, when the upper lens compactor is in the first compacted position (again, the "start" location of the upper lens compactor). In another embodiment, the multiple-lens IOL is disposed or stored in the compactor in the substantially unstressed condition described above, when the upper lens compactor is in the first compacted position.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An apparatus for compacting an intraocular lens having an optical axis intersecting a curved surface of a viewing element of the lens and passing through a geometric center of the lens, said apparatus comprising:
   a delivery lumen extending along an injection axis; and
   a lens compactor having a first configuration for retaining said intraocular lens in a substantially unstressed condition and a second configuration in which said compactor stresses said lens into an at least partially compacted condition by applying a compacting force in a direction generally orthogonal to the optical axis of the lens, said compactor responsive to a compactor actuator that is movable by a user to change said compactor from said first configuration to said second configuration, the lens remaining entirely outside of the delivery lumen in said second configuration,
   wherein said compactor comprises a compacting element which is moveable in a first direction generally parallel to said injection axis and in a second direction generally orthogonal to said injection axis.

2. The apparatus of claim 1, wherein said compacting force is applied to an edge of said lens and drives said lens towards a wall of said compactor, said wall located on a side of said lens opposite said edge.

3. The apparatus of claim 1, wherein said compacting force is applied to an outer face of the viewing element of said lens and drives said lens towards a wall of said compactor, said wall located on a side of said lens opposite said edge.

4. The apparatus of claim 1, further comprising a housing having an interior, said lens compactor being disposed within said housing interior.

5. The apparatus of claim 1, further comprising a driving member configured to force said lens out of said compactor when said lens is in said at least partially compacted condition.

6. The apparatus of claim 5, further comprising a delivery probe configured to receive the lens when driven from the compactor by the driving member.

7. The apparatus of claim 1, wherein said compactor further compacts the lens in the second configuration into a projection of said delivery lumen.

8. An apparatus for manipulating an accommodating intraocular lens having first and second viewing elements with respective optical axes that are substantially aligned, said apparatus comprising:
   an enclosure comprising an injection axis and a lens compactor having a first surface fixed relative to said injection axis and a second surface, said surfaces for engaging said first and second viewing elements;
   wherein said second surface is moveable in a first direction generally parallel to the injection axis to relatively move said viewing elements from a configuration wherein the optical axes of the first and second viewing elements coincide to a configuration wherein the optical axes are displaced apart relative to each other, said second surface further being moveable relative to the first surface in a second direction generally orthogonal to said injection axis after movement in the first direction;

wherein the first and second surfaces are disposed in the enclosure prior to movement of the second surface in the first or second direction.

9. The apparatus of claim 8, wherein at least one of said first and second viewing elements comprises an optic having refractive power.

10. The apparatus of claim 8 configured such that, in use, movement in the second direction occurs after movement in the first direction ceases.

11. An apparatus for manipulating an accommodating intraocular lens having first and second viewing elements with respective optical axes that are substantially aligned, said apparatus comprising:
   a lens compactor having a fixed surface and a moveable surface for engaging said first and second viewing elements, and at least one guide member associated with at least one of the fixed and moveable surfaces, the guide member(s) cooperating for relative sliding motion in a direction that is inclined with respect to the fixed surface, said moveable surface being moveable along a first path to relatively move said viewing elements from a configuration wherein the optical axes of the first and second viewing elements coincide to a configuration wherein the optical axes are displaced relative to each other, the first path being defined by the guide member (s), said compactor further comprising a first compacting element which applies force to the viewing elements while said optical axes are displaced such that the viewing elements are compacted against an opposing second compacting element, at least one of the first and second compacting elements being movable relative to the other of the first and second compacting elements along a second path different from the first path,
   wherein said first compacting element is moveable in a first direction generally parallel to an injection axis of said apparatus and in a second direction generally orthogonal to said injection axis.

12. The apparatus of claim 11, wherein at least one of said first and second viewing elements comprises an optic having refractive power.

13. The apparatus of claim 11 configured such that, in use, movement along the second path occurs after movement along the first path ceases.

14. An apparatus for delivering an intraocular lens having an optical axis intersecting a curved surface of a viewing element of the lens and passing through a geometric center of the lens, said apparatus comprising:
   a lens compactor, said intraocular lens disposed within said lens compactor and positioned such that said lens is compacted along a direction that is orthogonal to the optical axis upon actuation of said lens compactor; and
   a delivery probe in communication with said lens compactor, said delivery probe defining a delivery axis;
   a driving member disposed proximally of the delivery probe and configured to advance an intraocular lens through said probe along the delivery axis;
   said lens compactor comprising a compacting element which contacts said intraocular lens and is moveable from a home position relative to the driving member in a first direction generally parallel to said delivery axis and in a second direction generally orthogonal to said delivery axis;
   wherein when said compactor is in the home position, an intraocular lens disposed in said apparatus is positioned laterally from the delivery axis.

15. The apparatus of claim 14, wherein said intraocular lens comprises an accommodating intraocular lens.

16. The apparatus of claim 15, wherein said accommodating intraocular lens comprises first and second interconnected viewing elements.

17. The apparatus of claim 14, further comprising a sterile package surrounding said lens compactor and delivery probe.

18. The apparatus of claim 14 configured such, in use, that the lens compactor is moved along the second direction after movement along the first direction ceases.

* * * * *